United States Patent [19]

Aristoff

[11] 4,401,824

[45] Aug. 30, 1983

[54] BENZOPYRAN COMPOUNDS, DERIVATIVES OF PROSTAGLANDINS

[75] Inventor: Paul A. Aristoff, Portage, Mich.

[73] Assignee: The Upjohn Company, Kalamazoo, Mich.

[21] Appl. No.: 355,814

[22] Filed: Mar. 8, 1982

[51] Int. Cl.³ ............................................ C07D 311/78
[52] U.S. Cl. .................... 549/385; 549/305; 549/220; 549/214; 549/60; 549/421; 548/518; 548/517; 548/406; 546/269; 546/196; 546/14; 544/386; 544/150; 542/430; 542/429; 542/427; 542/426; 542/412; 568/380; 568/379; 424/283
[58] Field of Search ................ 549/385, 305, 220, 60, 549/214; 548/518, 517, 406; 546/269, 196, 14; 544/386, 150; 542/430, 429, 427, 426, 412

[56] References Cited

U.S. PATENT DOCUMENTS 4,306,075 12/1981 Aristoff .................................. 560/56

FOREIGN PATENT DOCUMENTS 24943 11/1981 European Pat. Off. .

Primary Examiner—Nicky Chan
Attorney, Agent, or Firm—L. Ruth Hattan; Robert A. Armitage

[57] ABSTRACT

Novel compounds of the following general formula:

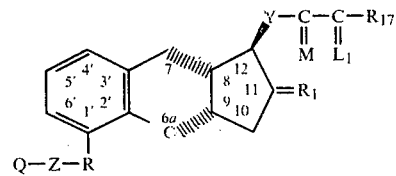

14 Claims, No Drawings

BENZOPYRAN COMPOUNDS, DERIVATIVES OF PROSTAGLANDINS

FIELD OF INVENTION

The present invention relates to novel benzopyran compounds which are prostaglandin derivatives, to processes for the preparation of said novel compounds and their use as pharmacological agents or as intermediates for the preparation of compounds useful as pharmacological agents. This invention also relates to chemical intermediates for preparing the novel benzopyran compounds described and claimed herein.

PRIOR ART

Related 6a methano compounds are described in U.S. Pat. No. 4,306,075. Also compounds having a 5-membered oxa containing ring are described in European Pat. No. 24–943 (Derwent No. 19801D).

SUMMARY OF THE INVENTION

The present invention consists of compounds of formula I wherein R is —$CH_2$— or —O—;

wherein Z is —$CH_2$—; —$CH_2CH_2$—; —$CF_2$—; —$CF_2CH_2$—; or wherein Z–R taken together is trans—CH=CH—$CH_2$— or trans—CH=CH—;

wherein Q is (1) —$COOR_5$, wherein $R_5$ is
 (a) hydrogen,
 (b) ($C_1$-$C_{12}$)alkyl,
 (c) ($C_3$-$C_{10}$)cycloalkyl,
 (d) ($C_7$-$C_{12}$)aralkyl,
 (e) phenyl optionally substituted with one, 2 or 3 chloro or ($C_1$-$C_4$)alkyl,
 (f) phenyl substituted in the para-position with —NHCOR$_6$, —COR$_7$, —OC(O)R$_8$ or —CH=N—NHCONH$_2$, wherein $R_6$ is methyl, phenyl, acetamidophenyl, benzamidophenyl or —NH$_2$; $R_7$ is methyl, phenyl, —NH$_2$, or methoxy; and $R_8$ is phenyl or acetamidophenyl;
 (g) phthalidyl,
 (h) 3-(5,5-dimethyl-1,3,2-dioxaphosphorinan-2-yl)-2-oxopropan-1-yl P-oxide,
 (i) 3-(5,5-di(hydroxymethyl)-1,3,2-dioxaphosphorinan-2-yl)-2-oxopropan-1-yl P-oxide, or
 (j) a pharmacologically acceptable cation;
(2) —$CH_2OH$;
(3) —$COL_2$, wherein $L_2$ is
 (a) an amino group of the formula —NR$_9$R$_{10}$ wherein $R_9$ is hydrogen or ($C_1$-$C_{12}$)alkyl and $R_{10}$ is
 (i) hydrogen
 (ii) ($C_1$-$C_{12}$)alkyl
 (iii) ($C_3$-$C_{10}$)cycloalkyl,
 (iv) ($C_7$-$C_{12}$)aralkyl
 (v) phenyl optionally substituted with one, 2 or 3 chloro, ($C_1$-$C_3$)alkyl, hydroxy, carboxy, ($C_2$-$C_5$)alkoxycarbonyl, or nitro,
 (vi) ($C_2$-$C_5$)carboxyalkyl,
 (vii) ($C_2$-$C_5$)carbamoylalkyl,
 (viii) ($C_2$-$C_5$)cyanoalkyl,
 (ix) ($C_3$-$C_6$)acetylalkyl,
 (x) ($C_7$-$C_{12}$)benzoylalkyl, optionally substituted by one, 2, or 3 chloro, ($C_1$-$C_3$)alkyl, hydroxy, ($C_1$-$C_3$)alkoxy, carboxy, ($C_2$-$C_5$)-alkoxycarbonyl, or nitro,
 (xi) pyridyl, optionally substituted by one, 2, or 3 chloro, ($C_1$-$C_3$)alkyl, or ($C_1$-$C_3$)alkoxy,
 (xii) ($C_6$-$C_9$)pyridylalkyl optionally substituted by one, 2, or 3 chloro, ($C_1$-$C_3$)alkyl, hydroxy, or ($C_1$-$C_3$)alkyl,
 (xiii) ($C_1$-$C_4$) hydroxyalkyl,
 (xiv) ($C_1$-$C_4$)dihydroxyalkyl,
 (xv) ($C_1$-$C_4$)trihydroxyalkyl;
 (b) cycloamino selected from the group consisting of pyrolidino, piperidino, morpholino, piperazino, hexamethyleneimino, pyrroline, or 3,4-didehydropiperidinyl optionally substituted by one or 2 ($C_1$-$C_{12}$)alkyl;
 (c) carbonylamino of the formula —NR$_{11}$COR$_{10}$, wherein $R_{11}$ is hydrogen or ($C_1$-$C_4$)alkyl and $R_{10}$ is other than hydrogen, but otherwise defined as above;
 (d) sulfonylamino of the formula —NR$_{11}$SO$_2$R$_{10}$, wherein $R_{11}$ and $R_{10}$ are defined in (c);
(4) —$CH_2NL_3L_4$, wherein $L_3$ and $L_4$ are hydrogen or ($C_1$-$C_4$)alkyl, being the same or different, or the pharmacologically acceptable acid addition salts thereof when Q is —$CH_2NL_3L_4$;
(5) —CN; or

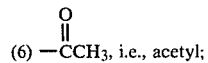

(6) —CCH$_3$, i.e., acetyl;

wherein $R_1$ is oxo, i.e., =O; H,H; α-OR$_{12}$,β-H; α-H,-β-OR$_{12}$; α-CH$_2$OR$_{12}$,β-H; α-H,β-CH$_2$OR$_{12}$ wherein $R_{12}$ is hydrogen or a hydroxyl protective group; or wherein Y is trans —CH=CH—, cis—CH=CH—, —$CH_2CH_2$—, or —C≡C—;

wherein M is α-OR$_{12}$,β-R$_{14}$; or α-R$_{14}$,β-OR$_{12}$, wherein $R_{12}$ is as defined above, and $R_{14}$ is hydrogen or methyl;

wherein L$_1$ is α-R$_{15}$,β-R$_{16}$; α-R$_{16}$,β-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;

wherein $R_{17}$ is (1) —$C_mH_{2m}CH_3$ wherein m is an integer of from one to 5,
(2) phenoxy optionally substituted by one, 2, or 3 chloro, fluoro, trifluoromethyl, ($C_1$-$C_3$)alkyl, or ($C_1$-$C_3$)alkoxy, with the proviso that not more than two substituents are other than alkyl and with the proviso that $R_{17}$ is phenoxy or substituted phenoxy, only when R$_{15}$ and R$_{16}$ are hydrogen or methyl, being the same or different;
(3) phenyl, benzyl, phenylethyl, or phenylpropyl optionally substituted on the aromatic ring by one, 2, or 3 chloro, fluoro, trifluoromethyl ($C_1$-$C_3$)alkyl, or ($C_1$-$C_3$)alkoxy, with the proviso that not more than two substituents are other than alkyl,
(4) cis—CHαCH—$CH_2C_3$,
(5) —($CH_2$)$_2$—CH(OH)—$CH_3$,
(6) —($CH_2$)$_3$—CH=C($CH_3$)$_2$,

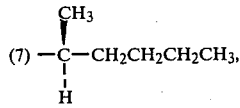

(7) —C—$CH_2CH_2CH_2CH_3$,

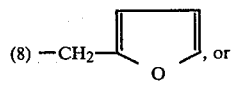

(8) —$CH_2$— , or (9) —CH$_2$— 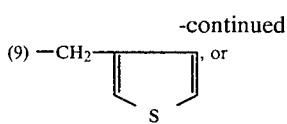, or wherein 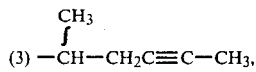 taken together is (1) (C$_4$–C$_7$)cycloalkyl optionally substituted by one to 3 (C$_1$–C$_5$)alkyl,
(2) 3-thienyloxymethyl, (3) $-\text{CH}-\text{CH}_2\text{C}\equiv\text{C}-\text{CH}_3$, with CH$_3$ branch, (4) —C≡C—C$_q$H$_{2q}$CH$_3$ wherein q is an integer of from 2 to 6, or
(5) —C$_p$H$_{2p}$CH=CH$_2$ wherein p is an integer of from 3 to 7; and individual optical isomers thereof.

The compounds of general Formula I wherein R$_{12}$ is hydrogen possess useful pharmacological properties as defined in detail hereinbelow and pharmacologically acceptable salts which may be formed with these compounds are a part of the present invention.

The compounds of Formulas II, XIII, XIX and XXII are useful as intermediates in the preparation of the compounds of Formula I, and in said formulas the substituent groups, Y, M, L$_1$, R$_{17}$, and R' have the same meanings as defined in Formula I, and R$_{33}$ is —CHO or —CH$_2$OR$_{12}$ wherein R$_{12}$ is hydrogen or a hydroxyl protecting group.

The intermediates of Formulas II and XIII wherein R$_{17}$ is

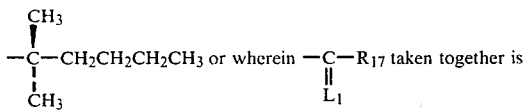

(a) $-\text{CH}-\text{CH}_2\text{C}\equiv\text{C}-\text{CH}_3$, with CH$_3$ branch, (b) —C≡C—C$_q$H$_{2q}$CH$_3$ wherein q is an integer of from 2 to 6, or
(c) —C$_p$H$_{2p}$CH=CH$_2$ wherein p is an integer of from 3 to 7, are also a part of the present invention.

DETAILED DESCRIPTION OF INVENTION

The compounds of the present invention are trivially named as derivatives of prostaglandin F$_1$ using in general the art-recognized system of nomenclature described by N. A. Nelson, J. Med. Chem. 17:911 (1974) for prostaglandins.

In the formulas herein, broken line attachments to a ring, i.e., (---), indicate substituents in the "alpha" (α) configuration, i.e., below the plane of said ring. A heavy solid line attachment to a ring, i.e., ( ◄■ ), indicates substituents in the "beta" (β) configuration, i.e., above the plane of said ring. The use of wavy lines (∼) herein indicates attachment of substituents in the alpha or beta configuration or attached in a mixture of alpha and beta configurations. Alternatively wavy lines will represent either an E or Z geometric isomeric configuration or the mixture thereof.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel compounds described herein. With regard to the divalent groups described above, i.e., R$_1$, M, and L$_1$ said divalent groups are defined in terms of an α-substituent and a β-substituent which means that the α-substituent of the divalent group is in the alpha configuration with respect to the plane of the C-8 to C-12 cyclopentane ring and the β-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety L$_2$ in the —COL$_2$ substituent group the definition (C$_1$–C$_{12}$)alkyl means that L$_2$ can be an alkyl group having from one to 12 carbon atoms. Additionally, any moiety so defined includes straight chain or branched chain groups. Thus (C$_1$–C$_{12}$)alkyl as set forth above includes straight or branched chain alkyl groups having from 1 to 12 carbon atoms and as additional illustration, when L$_2$ represents, for example, (C$_2$–C$_5$)carboxyalkyl, the alkyl moiety thereof contains from 1 to 4 carbon atoms and is a straight chain or a branched chain alkyl group.

The compounds wherein R is oxa, i.e., —O— and Z is —CH$_2$— are named as 9-deoxy-2',9α-epoxy-3-oxa-4,5,6-trinor-3,7-(1',3'-interphenylene)-PGF$_1$ compound. The compounds wherein each of R and Z$_3$ is —CH$_2$— are named as 9-deoxy-2',9α-epoxy-4,5,6-trinor-3,7-(1',3'-interphenylene)-PGF$_1$ compounds. When Z$_3$ is —CH$_2$CH$_2$— the compounds are further characterized as "2a-homo". When Z$_3$ is —CF$_2$— the compounds are further characterized as "2,2-difluoro" compounds. And when Z$_3$ is —CF$_2$CH$_2$— the compounds are further characterized as "2,2-difluoro-2a-homo". When Z$_3$R taken together is —CH=CH—CH$_2$— the compounds are named as "2a-vinylidene" compounds. When Z$_3$R is —CH=CH— the compounds are named as 2a-methinyl compounds.

When R$_{14}$ is methyl, the compounds are named as "15-methyl—" compounds. Further, except for compounds wherein Y is cis-—CH=CH—, compounds wherein the M moiety contains an hydroxyl in the beta configuration are additionally named as "15-epi—" compounds.

When Y is cis-—CH=CH—, and the M moiety contains an hydroxyl in the alpha configuration the compounds are named as "15-epi—" compounds. For a description of this convention of nomenclature for identifying C-15 epimers, see U.S. Pat. No. 4,016,184, issued Apr. 5, 1977, particularly columns 24–27 thereof.

The compounds of Formula I which contain —(CH$_2$)$_2$—, cis-—CH=CH—, or —C≡C— as the Y moiety, are accordingly referred to as "13,14-dihydro", "cis-13", or "13,14-didehydro" compounds, respectively.

When R$_{17}$ is straight chained —C$_m$H$_{2m}$—CH$_3$, wherein m is an integer of from one to 5, the compounds so described are named as "19,20-dinor", "20-nor", "20-methyl" or "20-ethyl" compounds when m is one, 2, 4 or 5, respectively. When R$_{17}$ is branched chain —C$_m$H$_{2m}$—CH$_3$, then the compounds so described are "17-, 18-, 19-, or 20-alkyl" or "17,17-, 17,18-, -17,19-, 17,20-, 18,18-, 18,19-, 18,20-, 19,19-, or 19,20-dialkyl" compounds when m is 4 or 5 and the unbranched portion of the chain is at least n-butyl, e.g., 17,20-dimethyl" compounds are described when m is 5 (1-methylpentyl).

When $R_{17}$ is phenyl and neither $R_{15}$ nor $R_{16}$ is methyl, the compounds so described are named as "16-phenyl-17,18,19,20-tetranor" compounds. When $R_{17}$ is substituted phenyl, the corresponding compounds are named as "16-(substituted phenyl)-17,18,19,20-tetranor" compounds.

When one and only one of $R_{15}$ and $R_{16}$ is methyl or both $R_{15}$ and $R_{16}$ are methyl, then the corresponding compounds wherein $R_{17}$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds respectively.

When $R_{17}$ is benzyl, the compounds so described are named as "17-phenyl-18,19,20-trinor" compounds. When $R_{17}$ is substituted benzyl, the corresponding compounds are named as "17-(substituted phenyl)-18,19,20-trinor" compounds.

When $R_{17}$ is phenylethyl, the compounds so described are named as "18-phenyl-19,20-dinor" compounds. When $R_{17}$ is substituted phenylethyl, the corresponding compounds are named as "18-(substituted phenyl)-19,20-dinor" compounds.

When $R_{17}$ is phenylpropyl, the compounds so described are named as "19-phenyl-20-nor" compounds. When $R_{17}$ is substituted phenylpropyl the corresponding compounds are named as "19-(substituted phenyl)-b 20-nor" compounds.

When $R_{17}$ is phenoxy and neither $R_{15}$ nor $R_{16}$ is methyl, the compounds so described are named as "16-phenoxy-17,18,19,20-tetranor" compounds. When $R_{17}$ is substituted phenoxy, the corresponding compounds are named as "16-(substituted phenoxy)-17, 18,19,20-tetranor" compounds. When one and only one of $R_{15}$ and $R_{16}$ is methyl or both $R_{15}$ and $R_{16}$ are methyl, then the corresponding compounds wherein $R_{17}$ is as defined in this paragraph are named as "16-phenoxy or 16-(substituted phenoxy)-18,19,20-trinor" compounds or "16-methyl-16-phenoxy- or 16-(substituted phenoxy)18,19,20-trinor" compounds, respectively.

When $R_{17}$ is cis—CH=CH—CH$_2$CH$_3$, the compounds so described are named as "cis-17,18-didehydro" compounds.

When $R_{17}$ is —(CH$_2$)$_2$—CH(OH)—CH$_3$, the compounds so described are named as "19-hydroxy" compounds.

When $R_{17}$ is —(CH$_2$)$_3$—CH=C(CH$_3$)$_2$, the compounds so described are named as "20-isopropylidene" compounds.

When $R_{17}$ is $$\begin{array}{c} CH_3 \\ | \\ -C-CH_2CH_2CH_2CH_3 \\ | \\ H \end{array}$$

the compounds so described are named as 17(S),20-dimethyl compounds.

When $R_{17}$ is 2-furylmethyl or 3-thienylmethyl, i.e., $$-CH_2-\!\!\!\underset{O}{\bigsqcup}\quad \text{or} \quad -\!\!\underset{S}{\overset{-CH_2-}{\bigsqcup}}$$

respectively the compounds so described are named as "17-(2-furyl)-18,19,20-trinor" compounds and "17-(3-thienyl)-18,19,20-trinor" compounds respectively.

When —C(L$_1$)—R$_{17}$ is $$\begin{array}{c} CH_3 \\ | \\ -CH-CH_2C\equiv C-CH_3, \end{array}$$

the compounds are named as "16-(R,S)methyl-18,19-tetradehydro" compounds.

When —C(L$_1$)—R$_{17}$ is optionally substituted cycloalkyl or 3-thienyloxymethyl, the compounds so described are named respectively 15-cycloalkyl-16,17,18,19,20-pentanor compounds and 16-(3-thienyl)oxy 17,18,19,20-tetranor compounds. The term 3-thienyloxymethyl means the moiety having the structure:

$$-CH_2-O-\!\!\underset{S}{\bigsqcup}$$

When —C(L$_1$)R$_{17}$ is —C≡C—C$_q$H$_{2q}$CH$_3$ wherein q is an integer of from 2 to 6 the compounds so described are named as "16,17-tetradehydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When —C(L$_1$)R$_{17}$ is —C$_p$H$_{2p}$CH=CH$_2$ wherein p is an integer of from 3 to 7 the compounds so described are named as "19,20-didehydro", "19,20-didehydro-18a,18b-dihomo", "19,20-didehydro-18a,18b,18c-trihomo", "19,20-didehydro-18a,18b,18c,18d-tetrahomo" compounds as the integer represented by p varies from 3 to 7 respectively. When at least one of $R_{15}$ and $R_{16}$ is not hydrogen then (except for the 16-phenoxy or 16-phenyl compounds discussed above) there are described the "16-methyl" (one and only one of $R_{15}$ and $R_{16}$ is methyl), "16,16-dimethyl" ($R_{15}$ and $R_{16}$ are both methyl), "16-fluoro" (one and only one of $R_{15}$ and $R_{16}$ is fluoro), "16,16-difluoro" ($R_{15}$ and $R_{16}$ are both fluoro) compounds. For those compounds wherein $R_{15}$ and $R_{16}$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is —CH$_2$OH, the compounds so described are named as "2-decarboxy-2-hydroxymethyl" compounds.

When Q is —CH$_2$NL$_3$L$_4$, the compounds so described are named as "2-decarboxy-2-aminomethyl" or "2-(substituted amino)methyl" compounds.

When Q is —COL$_2$, the novel compounds herein are named as amides. Further, when Q is —COOR$_5$ and R$_5$ is other than hydrogen the novel compounds herein are named as esters and salts.

When Q is CN the novel compounds herein are named as 2-decarboxy-2-cyano compounds.

When Q is $$\begin{array}{c} O \\ \| \\ -CCH_3 \end{array}$$

the novel compounds herein are named as 2-decarboxy-2-acetyl compounds.

Examples of phenyl esters substituted in the para position (i.e., Q is —COOR$_5$, R$_5$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is —COL$_2$) include the following:

(1) Amides within the scope of alkylamino groups of the formula-NR$_9$R$_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tertbutylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γdihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —$NR_{11}COR_{10}$ are methylcarbonylamide, ethylcarbonylamide, phenylcarbonylamide, and benzylcarbonylamide.

(4) Amides within the scope of sulfonylamino of the formula —$NR_{11}COR_{10}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of ($C_3$–$C_{10}$)cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of ($C_7$–$C_{12}$)aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

Examples of ($C_4$–$C_7$)cycloalkyl optionally substituted by one to 3 ($C_1$–$C_5$)alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Examples of substituted phenoxy, phenyl, phenylmethyl, i.e., benzyl, phenylethyl, or phenylpropyl of the $R_{17}$ moiety are (o-, m-, or p-)tolyl, (o-, m-, or p-)ethylphenyl, 4-ethyl-o-tolyl, 5-ethyl-m-tolyl, (o-, m-, or p-)propylphenyl, 2-propyl-(m- or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(m- or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)-methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 4-ethyl-o-tolyloxy, 5-ethyl-m-tolyloxy, (o-, m-, or p-)propylphenoxy, 2-propyl-(m- or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(m- or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3, 4, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenyl methyl, 4-ethyl-o-tolylmethyl, 5-ethyl-m-tolylmethyl, (o-, m-, or p-)propylphenylmethyl, 2-propyl-(m- or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(m- or p-)tolylmethyl, 4-fluoro-2,5-xylylmethyl, (2,4-, 2,5-, 2,6-, 3,4-, or 3,5-)difluorophenylmethyl, (o-, m-, or p-)tolylethyl, (o-, m-, or p-)ethylphenylethyl, 4-ethyl-o-tolylethyl, 5-ethyl-m-tolylethyl, (o-, m-, or p-)propylphenylethyl, 2-propyl-(m- or p-)tolylethyl, 4-isopropyl-2,6-xylylethyl, 3-propyl-4-ethylphenylethyl, (2,3,4-, 2,3,5-, 2,3,6-, or 2,4,5-)trimethylphenylethyl, (o-, m-, or p-)fluorophenylethyl, 2-fluoro-(m- or p-)tolylethyl, 4-fluoro-2,5-xylylethyl, (2,4-, 2,5-, 2,6- 3,4-, or 3,5-)difluorophenylethyl, (o-, m-, or p-)chlorophenylmethyl, 2-chloro-p-tolylmethyl, (3, 4, 5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl, (o-, m-, or p-)chlorophenylpropyl, 2-chloro-p-tolylpropyl, (3, 4, 5, or 6-)chloro-o-tolylpropyl, 4-chloro-2-propylphenylpropyl, 2-isopropyl-4-chlorophenylpropyl, 4-chloro-3,5-xylylpropyl, (2,3-, 2,4-, 2,5-, 2,6-, 3,4-, or 3,5-)dichlorophenylpropyl, 4-chloro-3-fluorophenylpropyl, (3- or 4-)-chloro-2-fluorophenylpropyl, (o-, m-, or p-)trifluoromethylphenylpropyl, (o-, m-, or p-)methoxyphenylpropyl, (o-, m-, or p-)ethoxyphenylpropyl, (4- or 5-)chloro-2-methoxyphenylpropyl, and 2,4-dichloro-(4- or 6-)methoxyphenylpropyl.

The group —$C_mH_{2m}CH_3$ wherein m is an integer of from one to 5 which $R_{17}$ may be represents straight or branched alkyl$C_1$-$C_5$ groups such as named hereinabove.

The terms phthalidyl; 3-(5,5-dimethyl-1,3,2-dioxaphosphorinan-2-yl)-2-oxopropan-1-yl P-oxide; and 3-(5,5-di(hydroxymethyl)-1,3,2-dioxaphosphorinan-2-yl)-2-oxopropan-1-yl P-oxide; which $R_5$ may represent in the —COOR$_5$ group mean the following respective moieties (a), (b) and (c):

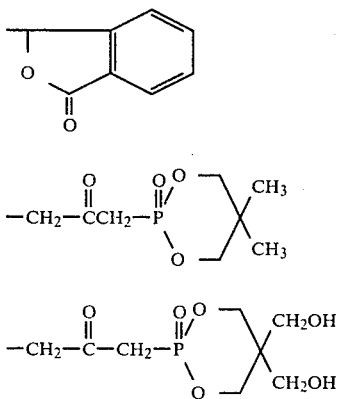

As indicated hereinabove R$_{12}$ is hydrogen or a protecting group. Those protective groups within the scope of R$_{12}$ are any group which replaces a hydroxy hydrogen and is neither attacked by nor is reactive to the reagents used in the transformations used herein as a hydroxy is and which is subsequently replaceable by hydrolysis with hydrogen in the preparation of the compounds of the present invention. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pp. 51–79 (1969). Those blocking groups which have been found useful include:

(a) tetrahydropyranyl;
(b) tetrahydrofuranyl;
(c) a group of the formula —C(OR$_{24}$)(R$_{18}$)—CH(R$_{19}$)(R$_{20}$), wherein R$_{24}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein R$_{18}$ and R$_{19}$ are alkyl of one to 4 carbon atoms, inclusive, phenyl, phenyl substituted with one, 2 or 3 alkyl of one to 4 carbon atoms, inclusive, or when R$_{18}$ and R$_{19}$ are taken together —(CH$_2$)$_a$— or when R$_{18}$ and R$_{19}$ are taken together to form —(CH$_2$)$_b$—O—(CH$_2$)$_c$, wherein a is 3, 4, or 5 and b is one, 2, or 3, and c is one, 2, or 3, with the proviso that b plus c is 2, 3, or 4, with the further proviso that R$_{18}$ and R$_{19}$ may be the same or different, and wherein R$_{20}$ is hydrogen or phenyl;
(d) silyl groups according to R$_{21}$, as qualified hereinafter; and
(e) an acyl protecting group such as alkanoyl of from 2 to 12 carbon atoms.

When the protective group R$_{12}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the R$_{12}$ protective group is tetrahydrofuranyl, 2,3-dihydrofuran is used, as described in the preceding paragraph, in place of the 2,3-dihydropyran.

When the R$_{12}$ protective group is of the formula —C(OR$_{24}$)(R$_{18}$)—CH(R$_{19}$)(R$_{20}$), wherein R$_{24}$, R$_{18}$, R$_{19}$, and R$_{20}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

R$_{21}$ is a silyl protective group of the formula —Si(G$_1$)$_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of —Si(G$_1$)$_3$ include trimethylsilyl, dimethylphenylsilyl, triphenylsilyl, t-butyldimethylsilyl, or methylphenylbenzylsilyl. With regard to G$_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to R$_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The R$_{12}$ protective groups as defined by (a) to (d) above are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

In preparing these acyl derivatives of a hydroxy-containing compound herein, methods generally known in the art are employed. Thus, for example, a C$_2$ to C$_{12}$ alkanoic acid or an anhydride thereof is reacted with the hydroxy-containing compound in the presence of a dehydrating agent, e.g. p-toluensulfonyl chloride or dicyclohexylcarbodiimide. Preferably, however, the acyl protecting group is introduced by use of the appropriate acyl halide, e.g., acetyl chloride, in the presence of a hydrogen halide scavenger, e.g. a tertiary amine such as pyridine, triethylamine or the like. The reaction is carried out under a variety of conditions, using procedures generally known in the art. Generally mild conditions are employed: 0°-60° C., contacting the reactants in a liquid medium (e.g., excess pyridine or an inert solvent such as benzene, toluene, or chloroform). The acylating agent is used either in stoichiometric amount or in substantial stoichiometric excess.

The acyl protective groups, according to $R_{12}$, are removed by deacylation. Alkali metal carbonate or hydroxide are employed effectively at ambient temperature for this purpose. For example, potassium carbonate or hydroxide in aqueous methanol at about 25° C. is advantageously employed.

The compounds of Formula I wherein $R_{12}$ is hydrogen produce certain prostacyclin-like pharmacological responses. Accordingly, the novel Formula I compounds wherein $R_{12}$ is hydrogen are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and antiasthma agents, and as antithrombotic agents as indicated below. The compounds of Formula I wherein $C(=L_1)R_{17}$ is $-CH(CH_3)CH_2C\equiv CCH_3$ are particularly useful in that said compounds possess an improved ratio of platelet aggregation to blood pressure lowering effects.

(a) Platelet Aggregation Inhibition

The compounds of Formula I wherein $R_{12}$ is hydrogen are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2-4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001-1.0 μg per ml of whole blood. These compounds, i.e., the compounds of Formula I wherein $R_{12}$ is hydrogen are useful in the treatment of peripheral vascular diseases, in the same manner as described in U.S. Pat. No. 4,103,026.

(b) Gastric Secretion Reduction

Compounds of Formula I wherein $R_{12}$ is hydrogen are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 μg to about 20 μg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula I wherein $R_{12}$ is hydrogen are also useful in reducing the undesirable gastrointestinal effects resulting from systemic administration of anti-inflammatory prostaglandin synthetase inhibitors, and are useful for that purpose by concomitant administration of said compounds of Formula I and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula I compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula I wherein $R_{12}$ is hydrogen are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formula I compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula I compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a cosolvent, such as ethanol, flavoring materials and stabilizers. Suitable means to employ the aerosol inhalation therapy technique are described fully in U.S. Pat. No. 3,868,691, for example.

When Q is —COOR$_5$, the novel Formula I compounds so described are used for the purposes described above in the free acid form, in ester form, or in pharmacologically acceptable salt form. When the ester form is used, the ester is any of those within the above definition of R$_5$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula I for the purposes described above are those with pharmacologically acceptable metal cations, ammonia, amine cations, or quaternary ammonium cations. Illustrative pharmacological acceptable cations which R$_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is —CH$_2$NL$_3$L$_4$, the Formula I compounds so described are used for the purposes described in either free base of pharmacologically acceptable acid addition salt form.

The acid addition salts of the 2-decarboxy-2-aminomethyl- or 2-(substituted aminomethyl)-Formula I compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula I with the stoichiometric amount of the acid corresponding to the pharmacologically acceptable acid addition salt.

The compounds of Formula I wherein R$_{12}$ is a protecting group are useful as intermediates to the compounds of Formula I wherein R$_{12}$ is hydrogen.

To obtain the optimum combination of biological response specificity, potency, and duration of activity, certain compounds within the scope of this invention are preferred. Preferred compounds of the present invention are those of Formula I wherein Y is —CH$_2$CH$_2$—, —C≡C— or trans—CH=CH— and/or Q is —COOR$_5$ or —COL$_2$ are preferred especially when R$_5$ is hydrogen, methyl, ethyl, or a pharmacologically acceptable cation such as sodium, and when each of R$_9$ and R$_{10}$ of the L$_2$ substituent moiety is hydrogen. Also preferred are compounds of Formula I wherein R$_{17}$ is —C$_m$H$_{2m}$CH$_3$, benzyl, phenoxy, 3-thienylmethyl, or phenyl or wherein —C(L$_1$)R$_{17}$ taken together is cyclohexyl, 3-thienyloxymethyl or 3-ethylcyclobutyl, or —CH(~CH$_3$)CH$_2$C≡CCH$_3$ are especially preferred. Also compounds wherein R$_{17}$ is C$_m$H$_{2m}$CH$_3$ and each of R$_{15}$ and R$_{16}$, which make up the L$_1$ substituent, are fluoro are preferred. Of these preferred compounds those wherein Z is —CH$_2$— are more preferred and compounds wherein R is —O—, i.e., oxa, are most preferred. Also compounds wherein $R_1$ and M are α-$OR_{12}$,β-H wherein $R_{12}$ is hydrogen are more preferred.

As indicated hereinabove the hydroxyl groups at positions C-11 and C-15 of the compounds of the present invention may be protected by various groups generally employed in the art and protection of the hydroxyl functions is generally desirable or necessary during the preparation of the compounds. Although any of the various protecting groups described herein may be employed those preferred are tetrahydropyranyl (THP), tetrahydrofuranyl (THF), and tert-butyldimethylsilyl or tert-butyldiphenylsilyl. Of course it may be useful or desirable to utilize protecting groups which may be selectively hydrolyzed. Also, when $R_{17}$ is —$(CH_2)_2CH(OH)$—$CH_3$ the hydroxyl group at C-19 generally is protected by the same type of groups utilized to protect the C-11 and C-15 hydroxyl groups during the preparation of said compounds and subsequently deprotected by hydrolysis as described herein.

The preparation of the compounds of Formula I is depicted in Charts A, B and C hereof. Chart A depicts the preparation of the compounds of Formula I wherein R is —$CH_2$—. In Chart A the various substituent groups $R_1$, Y, M, $L_1$, $R_{17}$, and $R_{12}$ have the meanings defined in Formula I; the group Z' is —$CH_2$—, —$CH_2CH_2$, —$CF_2$—, or —$CF_2CH_2$—; the group Q' is the same as Q in Formula I only Q' is other than —$CH_2OH$; and W has the meaning defined in Chart A.

By the general procedures of D. R. Morton and J. L. Thompson, J. Org. Chem. 43, 2102 (1978) a 2-methylenecyclopentanone of Formula II is added at low temperature, e.g., −40° to −80° C., to a cuprate reagent derived from the treatment of a compound of Formula III with t-butyllithium, copper iodide, and a trialkylphosphine, such as, tri-n-butylphosphine to give a methoxy substituted interphenylene-cyclopentanone of Formula IV. The cyclopentanone of Formula IV is reduced to the corresponding cyclopentanol by generally known procedures, e.g., using a hydride reducing agent, such as, sodium borohydride in methanol or ethanol, after which the interphenylene methyl ether is hydrolyzed to the corresponding phenol by generally known means, e.g., by using a lithium alkylsulfide, e.g., butyl mercaptide in hexamethylphosphoramide by the general procedures described by S. C. Welch and A.S.C.P. Rao, Tetrahedron Lett. 505 (1977) to give the compounds of Formula V. The methyl ether may also be hydrolyzed using lithium diphenylphosphide in, e.g., tetrahydrofuran according to the procedure of R. E. Ireland, et al., J. Am. Chem. Soc. 95, 7829 (1973). Intramolecular cyclization of the phenol of Formula V to the benzopyran derivative of Formula VI is achieved using a trisubstituted phosphine, e.g., triphenyl phosphine and diethyl azodicarboxylate which is an adaptation of the procedure of Bittner, Chem. Inc. (London), 281 (1975) and Manhas, J. Chem. Soc. Perkin Trans. 1, 461 (1975). The primary alcohol $R_{12}$ protecting group and any protecting group which may be present at positions C-11, C-15 or C-19 are removed by hydrolysis as generally described hereinbefore to give compounds of Formula VII. The alcohols of Formula VII are useful to derive the corresponding compounds wherein the C-1 position substituent is other than —$CH_2OH$. During such C-1 position conversions it is generally desirable to have any hydroxy groups at C-11, C-15 or C-19 protected with $R_{12}$ groups by procedures described hereinabove.

Oxidation of the primary alcohol of Formula VII to the C-1 carboxylic acid of Formula VIII may be achieved by using platinum and oxygen by generally known procedures. Alternatively the primary alcohol of Formula VII may be selectively protected with a silyl protecting group, e.g., by treatment with one equivalent of t-butyldimethylsilyl chloride and any secondary alcohol which may be present at positions C-11, C-15 and C-19 is then protected with an $R_{12}$ group other than a silyl protecting group, e.g., acetyl after which the silyl ether is hydrolyzed with fluoride ion and the resulting primary alcohol oxidized to the C-1 carboxy using Jones reagent by known procedures. Following the oxidation step any secondary alcohol protecting groups are removed by hydrolysis. The thus obtained C-1 carboxylic acids of Formula VIII can be converted to the various ethers and amides as defined in Formula I, and the amides can be reduced to the corresponding amines, i.e., compounds wherein Q' is —$CH_2NL_3L_4$, by using lithium aluminum hydride as generally described in U.S. Pat. No. 4,073,808.

Also, the alcohols of Formula VII can be oxidized to the corresponding carboxaldehyde which upon treatment with a salt of hydroxylamine gives the oxime which is dehydrated to give the nitrile, i.e., Formula VIII compounds wherein Q' is —CN. The C-1 nitriles of Formula VIII may also be obtained by dehydration of the corresponding amide. By treatment of the nitrile with methyl lithium or a methyl Grignard the corresponding imine is obtained which is hydrolyzed with aqueous acid to the C-1 acetyl, i.e., Q' is

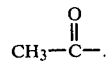

Also the acetyl derivatives are obtained by treating the C-1 carboxaldehyde with methyl lithium or methyl Grignard followed by oxidation using, e.g., Jones or Collins reagents. The various conversions at the C-1 position to obtain the compounds of Formula VIII are all known in the art. See, e.g., G.B. Pat. No. 2,013,661.

The compounds of Formula VIII wherein Z' is —$CH_2$— or —$CH_2CH_2$— and Q' is a carboxylic acid ester, e.g., a lower alkyl ester such as the methyl ester, are useful in the preparation of the compounds of Formula I wherein —Z—R— taken together is trans—$CH$=$CH$— or trans—$CH$=$CHCH_2$— as depicted in Chart B wherein pH is phenyl, s is zero or one and W' has the meaning defined in Chart B. The C-1 acid ester of Formula IX is treated with lithium amide base and phenylselenyl chloride to give the corresponding α-phenylselenyl derivatives (Formula X) which are converted to the trans-vinyl derivatives (Formula XI) by, e.g., the general procedures described in U.S. application G.B. No. 2,017,699. The compounds of Formula XI can be converted to the C-1 free acids, i.e., Formula XII where Q is —COOH, from which other esters or amides and in turn amines and nitriles can be formed as generally described hereinabove in connection with the preparation of the compounds of Formula VIII in Chart A. The C-1 carboxylic acids of Formula XII also can be reduced to the corresponding alcohol, i.e., Q is —$CH_2OH$, by, for example, refluxing with lithium aluminum hydride in an ether solvent. The alcohol thus obtained can be utilized to prepare the corresponding nitrile via the oxime and the C-1 acetyl derivatives as described hereinabove in reference to compounds of Formula VIII.

The preparation of the compounds of Formula I wherein R is —O— is depicted in Chart C hereof. In Chart C, the groups $R_1$, Y, M, $L_1$, $R_{17}$, Q and $R_{12}$ have the meanings defined in Formula I, Z' and alkyl are defined below and $W_2$ is as defined in Chart C. The phenol of Formula XIII is treated with one equivalent of base, e.g., sodium hydride and an appropriate alkyl halo alkanoate, e.g., alkyl bromo alkanoate of the formula BrZ'—COOalkyl wherein alkyl has, e.g., from 1 to 4 carbon atoms and is straight or branched and Z' is —CH$_2$—, —CH$_2$CH$_2$—, —CF$_2$—, or —CH$_2$CF$_2$— to give the ω-carboxyalkyl ether of Formula XIV which can be used to prepare the corresponding compounds depicted by Formula XV wherein the C-1 position group is other than a lower alkyl carboxylate, i.e., Q is as defined in Formula I. These various conversions at the C-1 position are carried out in the same manner as described hereinabove in relation to the compounds of Formula VIII in Chart A and as noted hereinbefore during such conversions it may be useful to have any hydroxyl groups at C-11, C-15 or C-19 protected by an $R_{12}$ group which may ultimately be removed by means described hereinabove.

C-1 alcohol compounds of Formula VII wherein Z' is —CH$_2$— may be used to prepare the C-1 carboxylic acids of Formula VIII wherein Z' is —CH$_2$CH$_2$—. The Formula VII primary alcohol is selectively activated with a leaving group, i.e., is converted to the mesylate or tosylate by treatment with one equivalent of methanesulfonyl chloride or p-toluenesulfonyl chloride at lower temperatures by generally known procedures. Treatment with sodium cyanide or potassium cyanide at elevated temperatures in a dipolar aprotic solvent results in displacement of the tosylate or mesylate group to give the corresponding C-1 nitrile derivative. Hydroxide hydrolysis of the nitrile by procedures known in the art gives the Formula VIII compounds wherein Q' is COOH and Z' is —CH$_2$CH$_2$—.

The compounds of Formula XIII in Chart C are prepared in a manner analogous to that described in Chart A for the preparation of the compounds of Formula VI. By substituting a compound of Formula XVI (see Formula Chart) for compounds of Formula III in Chart A and following the procedure therein described for the preparation of Formula VI compounds one obtains compounds of Formula XVII (Chart C) which are hydrolyzed by fluoride mediated or acid hydrolysis to the compounds of Formula XIII by generally known procedures.

In preparing the compounds of Formula III (see Chart A) wherein Z' is —CH$_2$— or —CH$_2$CH$_2$—, 6-allyl-2-bromophenol, which is a known compound and is obtained according to the procedure of C. D. Hurd and C. N. Webb, J. Am. Chem. Soc. 941 (1936), is alkylated using methyl iodide by generally known procedures to give the corresponding methyl ether, i.e., the compound depicted as Formula D-1 in Chart D hereof. By hydroboration-oxidation of the D-1 olefin by treatment with a hindered borane followed by oxidation with hydrogen peroxide and hydroxide by generally known procedures the alcohol of D-2 is obtained which is converted to the protected alcohol, D-3, wherein $R_{12}$ has the meaning defined in Formula I by procedures described herein. The alcohol of D-2 can be used to obtain Formula III compounds wherein Z' is —CH$_2$CH$_2$— by activation of the alcohol with a leaving group, e.g., $R_{13}$ is mesyl or tosyl by treatment with methanesulfonyl chloride or p-toluenesulfonyl chloride followed by cyanide displacement by treatment with sodium cyanide or potassium cyanide in a dipolar aprotic solvent at elevated temperatures to give the compound of D-5. Hydroxide hydrolysis of the nitrile by generally known procedures gives the acid of D-6 which is reduced to the alcohol (D-7) using, e.g., lithium aluminum hydride or diborane. The alcohol is then protected as described hereinbefore with an $R_{12}$ protecting group.

The compounds of Formula III wherein Z' is —CF$_2$— or —CF$_2$CH$_2$— are prepared as depicted in Chart E. By oxidizing 1-allyl-3-bromo-2-methoxybenzene (E-1) using, e.g., ozone followed by dimethyl sulfide work-up or by using methyl periodate one obtains the aldehyde E-3 wherein u is the integer one. By hydroboration-oxidation of the olefin E-1 by treatment with a hindered borane, such as 9-borobicyclononane, followed by treatment with hydrogen peroxide and hydroxide one obtains 3-bromo-2-methoxyphenylpropanol of E-2. The E-2 alcohol is oxidized to the aldehyde of E-3 wherein u is the integer 2 by standard procedures, e.g., using Collins or Jones reagent. Dithiane addition to the aldehydes of E-4 is accomplished by treatment with lithium dithiane according to the general procedure of D. Seebach and E. J. Corey, J. Org. Chem. 40, 231 (1975) to give compounds of E-4 which are oxidized using Jones or Collins reagents by standard procedures to the ketone of E-5. Dithiane hydrolysis of the E-5 ketone gives the oxalyl derivative E-6. Dithiane hydrolysis is achieved for example by treatment with silver nitrate in aqueous ethanol according to the procedure of C. A. Reece, et al., Tetrahedron 24, 4249 (1968) or by treatment with N-chlorosuccinimide and silver nitrate in acetonitrile and water according to the procedure of E. J. Corey, et al., J. Org. Chem. 36, 3553 (1971). Mild oxidation using silver nitrate or air oxidation of the oxalyl derivative gives the 2-ketoalkanoic acid of E-7 which is esterified by well known procedures., e.g., treatment with an acidic lower alkanol, such as, methanol, or by treatment with diazomethane to give E-8 compounds. The ester of E-8 is fluorinated using diethylaminosulfurtrifluoride by the general procedure of W. J. Middleton, et al., J. Org. Chem., 45, 2883 (1980) to give the 2,2-difluoroalkanoic acid ester of E-9. The difluoro E-9 compound is reduced to the alcohol using, e.g., diisobutyl aluminum hydride by standard procedures after which the alcohol is protected with an $R_{12}$ protecting group by means described hereinbefore.

The compounds of Formula XVI are prepared by treating the olefin of Formula D-1 (See Chart D) with base, e.g., potassium t-butoxide in t-butanol to give a compound of Formula D-9. A compound of formula D-9 is then ozonized for example with ozone followed by dimethyl sulfide work-up or by treatment with methyl periodate by well known procedures to give 3-bromo-2-methoxybenzaldehyde which is treated with a peracid, such as peracetic acid or perbenzoic acid or is treated with hydrogen peroxide followed by treatment with hydroxide, such as sodium or potassium hydroxide or potassium carbonate in a lower alkanol under the conditions of a Baeyer-Villiger reaction to give 3-bromo-2-methoxyphenol which is converted to a suitable OR$_{12}$ protected derivative by means described hereinbefore, e.g., by treatment with dihydropyran in acid to give the compound of Formula XVI.

The 2-bromo-2-methoxyphenol obtained above also can be treated with a base, e.g., sodium hydride and a protected ω-halo, e.g., bromo, alkanol of the formula $BrCH_2(CH_2)_s$—$CH_2OR_{12}$ wherein s is zero or one and $R_{12}$ has the meaning defined hereinbefore to give a compound of Formula XVIII which when substituted for the compounds of Formula III in Chart A and the procedures defined therein for the preparation of compounds of Formulas VII and VIII are followed results in compounds of Formula I wherein R is oxa and Z is —$CH_2$— or —$CH_2CH_2$—.

The compound of Formula XVIII wherein s is zero can also be prepared by treating 3-bromo-2-methoxyphenol with methyl bromoacetate to give 3-bromo-2-methoxyphenoxyacetic acid methyl ester which is reduced to the alcohol using, e.g., diisobutylaluminum hydride with subsequent protection of the alcohol with an $R_{12}$ protecting group as generally described hereinbefore.

The compounds of Formula XVI may additionally be prepared by protecting 2-methoxyphenol with an $R_{12}$ protecting group followed by treating with an alkyl lithium, e.g., n-butyllithium in hexane and tetramethylethylenediamine and quenching with bromine by the general procedures of G. Schill and E. Logeman, Chem. Ber. 106, 2910 (1973).

The compounds of Formula II are known in the art or are prepared by procedures generally known in the art. For example, the preparation of many of the compounds of Formula II is described in U.S. Pat. No. 4,181,798 and in particular in columns 7, 8 and 13–15 the pertinent portions of which are incorporated herein by reference. The starting materials used in preparing the compounds of Formula II are prepared as depicted in Chart F. Compounds of Formula F-1 wherein $R_1$ has the meaning defined in Formula I, which compounds are known in the art, are treated with the anion of an alkyl phosphonate of Formula F-2 wherein alkyl is a lower alkyl group such as methyl, ethyl, or n-propyl, and $L_1$ and $R_{17}$ have the meanings defined in Formula I, under the conditions of a Wittig reaction to give a ketone intermediate corresponding to Formula F-3 wherein $W^5$ is the group trans-CH=CH—C—C—$R_{17}$
        ‖  ‖
        O  $L_1$ which is then reduced by dissolving metal hydride reduction to the α- or β-alcohol as defined by M in Formula I to give compounds of Formula F-3 wherein $W^5$ is the group trans-CH=CH—C—C—$R_{17}$
        ‖  ‖
        $M_1$ $L_1$ wherein $M_1$ is α—OH,β—H or α—H,β—OH and wherein $L_1$ and $R_{17}$ have the meanings defined in Formula I. The thus obtained trans-vinyl compounds can be hydrogenated to give corresponding compounds of Formula F-3 wherein $W^5$ is the group

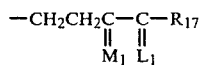

or can be halogenated followed by tetradehydrohalogenation to give the corresponding compounds of Formula F-3 wherein $W^5$ is the group

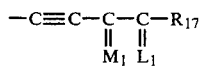

Hydrogenation of the thus obtained acetylene containing compounds with a Lindlar catalyst give the corresponding cis-vinyl compounds, i.e., Formula F-3 wherein $W^5$ is the group

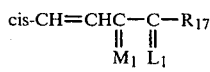

The compounds of Formula F-3 are also prepared by treating a compound of Formula F-1 with a phosphine of the formula $(alkyl)_3$—P=CHCHO under the conditions of a Wittig reaction to give the corresponding compounds of Formula F-3 wherein $W^5$ is trans-vinyl aldehyde group of the formula trans—CH=CHCHO which is reduced to the corresponding trans-vinyl alcohol, i.e., Formula F-3 wherein $W^5$ is trans—CH=CHCH$_2$OH. The trans-vinyl alcohol can be hydrogenated to give Formula F-3 compounds wherein $W^5$ is the group —$CH_2CH_2CH_2OH$, or the trans-vinyl alcohol can be halogenated then tetradehydrohalogenated to give the corresponding acetylene alcohol, i.e., compounds of Formula F-3 wherein $W^5$ is the group —C≡CCH$_2$OH. Hydrogenation of the acetylene alcohol with a Lindlar catalyst gives the corresponding cis-vinyl alcohols, i.e., Formula F-3 compounds wherein $W^5$ is the group cis—CH=CHCH$_2$OH.

The thus obtained alcohols, i.e., compounds of Formula F-3 wherein $W^5$ is trans—CH=CHCH$_2$OH, —$CH_2CH_2CH_2OH$, —C≡CCH$_2$OH or cis—CH=CHCH$_2$OH are oxidized to the corresponding aldehydes then treated with a Grignard reagent of the formula halo MgCpH$_{2p}$CH=CH$_2$, wherein halo is a halogen or an alkyl lithium of the formula LiCpH$_{2p}$CH=CH$_2$, or an acetylide anion of the formula —C≡CCpH$_{2p}$CH$_3$ or an anion of the formula LiCHCH$_2$C≡CCH$_3$
|
CH$_3$ to give compounds of Formula F-1 wherein $W^5$ is

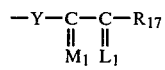

wherein Y, $L_1$ and $R_{17}$ have the meanings defined in Formula I and $M_1$ is α—OH,β—H or α—H,β—OH.

To prepare compounds of Formula F-3 wherein $R_{14}$ of the M substituent group is —CH$_3$ the corresponding C-15 alcohol derivatives are oxidized to the corresponding C-15 alcohol derivatives are oxidized to the corresponding C-15 ketone then treated with methyl lithium or a methyl Grignard by procedures known in the art.

The compounds of Formula F-2 are prepared by addition of the anion of a dialkyl methyl phosphonate of the formula

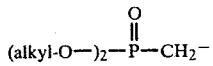

wherein alkyl is, e.g., methyl, ethyl, propyl or butyl with an ester of the formula

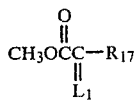

wherein $L_1$ and $R_{17}$ have the meanings defined in Formula I by procedures well known in the art.

The compounds of Formula I wherein R is oxa can also be prepared utilizing a compound of Formula XIX as depicted in Chart G. Wherein $R_1$ has the meaning defined in Formula I, $R_{33}$ is —CHO or —CH$_2$OR$_{12}$, and $R_{12}$ is a protecting group as defined hereinbefore. By substituting a compound of Formula XIX for compounds of Formula XIII in Chart C and following the procedure described for preparing compounds of Formula XIV from the compounds of Formula XIII one obtains the compounds of Formula XX wherein $R_1$ and $R_{33}$ are defined above and Z' is —CH$_2$—, —CH$_2$CH$_2$—, —CF$_2$—, or —CF$_2$CH$_2$—. It may be useful to protect the phenol hydroxy and the primary alcohol selectively. For example, the phenol may be protected with a silyl group or defined by $R_{21}$ and the alcohol with THP or some other $R_{12}$ protecting group other than a silyl group. The compouands of Formula XX are then converted to the compounds of Formula XXI which are then converted to the compounds of XXII by the same general procedures described hereinabove for the preparation of compounds of Formula F-3 and XV, respectively.

The compounds of Formula XX wherein $R_{33}$ is CHO are also useful in preparing the compounds of Formula I. The compounds of Formula XX are converted to the compounds of Formula I by the same general procedures described hereinabove for the preparation of the compounds of Formula F-3. The compounds of Formula XX wherein $R_{33}$ is —CH$_2$OR$_{12}$ are useful in making conversions of the various XXII C-1 groups represented by Q.

The compounds of Formula XIX and Formula XX wherein $R_{33}$ is —CHO are prepared by ozonolysis, e.g., ozone treatment followed by dimethyl sulfide work-up, of compounds of Formula XVII and Formula I respectively wherein in each the group Y is —CH═CH—. Reduction of the compounds of Formula XIX and XX wherein $R_{33}$ is —CHO by, e.g., use of sodium borohydride gives the corresponding primary alcohol which can be protected with an $R_{12}$ group by procedures described hereinbefore.

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., Q is —COOR$_5$ and $R_5$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift No. 2,535,693, and Derwent Farmdoc No. 16828X.

The phthalidyl esters are obtained by treating the corresponding acid with a phthalidyl halide such as the bromide in, e.g., dimethylformamide in the presence of an amine base. The phosphoranyl esters are obtained by treating the corresponding acid with a 1-halo derivative, e.g., the 1-chloro derivative of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is —COL$_2$) are prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the acids are prepared is, first, by transformation of such free acids to corresponding mixed acid anhydrides. By this procedure, the carbacyclin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to $20°$ C.

Thereafter, the mixed anhydride is converted to the corresponding amido or cycloamido derivatives by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the presently disclosed carbacyclin compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure carbacyclin sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about $0°$ C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation if inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(a) 6-Allyl-2-bromo-phenol

A degassed solution of o-bromophenol (4.04 g, 2.6 ml, 23.34 mmol) in acetone (30 ml) is treated at ambient temperature under an inert atmosphere with allyl bromide (3.39 g, 2.42 ml, 28.0 mmol) and anhydrous potassium carbonate (5.48 g, 39.68 mmol). The resulting yellow suspension is stirred at reflux for 3 hours, cooled and filtered. The filtrate is concentrated in vacuo, then partitioned between diethyl ether and cold water. The layers are separated and the aqueous layer extracted with diethyl ether. The ether extract is washed with saturated sodium bicarbonate, then twice with brine, dried over magnesium sulfate, filtered and concentrated to give 5.46 g of yellow oil.

The crude product is distilled at 0.82 mm and collected at $73°$–$75°$ C. to give 1-allyloxy-2-bromobenzene as a colorless oil.

Degassed 1-allyloxy-2-bromobenzene (3.34 g, 25.68 mmol) is stirred under nitrogen while being heated at $210°$–$223°$ C. for 2 hours. The reaction is cooled to $\sim 5°$ C., diluted with ether and extracted with 1 N sodium hydroxide ($2\times20$ ml). The alkaline (aqueous) layer is acidified with cold, 1 N hydrochloric acid and extracted with ether ($3\times100$ ml). The acidic ether extract is washed with brine ($2\times100$ ml), dried over magnesium sulfate, filtered and concentrated to give 2.16 g of brown oil.

The crude product is distilled at 0.78 mm at 74°–90° C. (oven temperature) to give 1.96 g of the title product.

TLC (Silica Gel GF): $R_f$=0.20 in hexane; $R_f$=0.43 in ethyl acetate/hexane.

(b) 3-Allyl-2-methoxy-1-bromobenzene

A solution of 6-allyl-2-bromophenol (4.84 g, 22.72 mmol) in dry t-butyl alcohol (11.5 ml) and dry glyme (28 ml) is added to a suspension of potassium t-butoxide (2.65 g, 23.63 mmol) in dry t-butyl alcohol (24 ml) at ambient temperature under an inert atmosphere. The resulting greenish yellow suspension is treated with methyl iodide (5 ml) and stirred for 3.5 hours. The reaction gradually turns from yellow to light brown, and a precipitate forms within 30 minutes. After 3.5 hours, the reaction is diluted with cold water (200 ml) and extracted with diethyl ether (3×175 ml). The organic extract is washed with brine (2×200 ml), dried over magnesium sulfate, filtered and concentrated to give 4.16 g of brown oil.

The crude product is chromatographed on basic alumina eluting with 2% ethyl acetate in hexane to give 3.72 g of brown oil.

Distillation of the product at 80°–90° C. (oven temperature) at 0.21 mm gives 3.58 g of 2-allyl-6-bromoanisole.

TLC (Silica Gel GF): $R_f$=0.53 in 5% ethyl acetate/hexane.

(c) 2-Methoxy-3-[3'-(hydroxypropyl)]-1-bromobenzene

A degassed solution of 2-allyl-6-bromoanisole (3.53 g, 15.5 mmol) in dry tetrahydrofuran (225 ml) is cooled to 0° C. under an inert atmosphere and treated with 0.5 M 9-borobicyclo[3.3.1]nonane in tetrahydrofuran (50 ml). The resulting colorless solution is stirred for 1 hour at 0° C. and is permitted to warm to ambient temperature slowly overnight. After 18 hours the solution is cooled to 0° C., treated with 30% hydrogen peroxide (21 ml) followed by 3 N potassium hydroxide (aqueous, 21 ml). There is effervescence upon the addition of hydrogen peroxide, and the colorless solution becomes turbid upon the addition of potassium hydroxide. The resulting suspension is stirred for 30 minutes at 0° C. then for 2 hours while warming to ambient temperature. The suspension is poured into ice-cold brine (300 ml) and extracted with ethyl acetate (3×200 ml). The combined ethyl acetate extracts are washed with brine (300 ml), dried over magnesium sulfate, filtered and concentrated to a brown oil (8.3 g). The crude product is chromatographed on 610 g of silica gel in 25% ethyl acetate in hexane. The column is eluted with 6 liters of 25% ethyl acetate in hexane and 2 liters of 50% ethyl acetate in hexane to give 2.86 g of the title product.

TLC (Silica Gel GF): $R_f$=0.08 in 20% ethyl acetate/hexane; $R_f$=0.11 in 25% ethyl acetane/hexane.

(d) 2-Methoxy-3-[3'-(tetrahydropyranyloxypropyl]-1-bromobenzene

A degassed solution of 2-methoxy-3[3'-(hydroxypropl]-1-bromobenzene (2.78 g, 11.67 mmol) in methylene chloride (30 ml) is treated at ambient temperature under an inert atmosphere with dihydropyran (10 ml, 110 mmoles) followed by saturated pyridinehydrochloride/methylene chloride (1.2 ml). The resulting solution is permitted to stir for 18 hours, diluted with methylene chloride (150 ml) and washed with saturated sodium bicarbonate (aqueous, 150 ml). The aqueous wash is extracted with methylene chloride (150 ml), and the organics are washed with brine (150 ml), dried over magnesium sulfate, filtered and concentrated to 6.42 of amber oil. The crude product is chromatographed on 570 g of silica gel in 10% ethyl acetate in hexane. The column is eluted with 2 liters each of 10% and 15% ethyl acetate in hexane to give 3.66 g of the title compound.

NMR (CDCl$_3$, TMS) δ: 1.33–2.10 (m, 8H), 2.75 (t, 2H), 3.25–4.03 (m, 4H), 3.80 (s, 3H), 4.53 (m, 1H), 6.73–7.45 (m, 3H).

Infrared (film): 3354, 2998, 2940, 2870, 2826, 1565, 1466, 1452, 1421, 1292, 1254, 1227, 1170, 1125, 1083, 1059, 1039, 1004, 919, 798, 777, 753 cm$^{-1}$.

TLC (Silica Gel GF): $R_f$=0.20 in 10% ethyl acetate/hexane; $R_f$=0.34 in 15% ethyl acetate/hexane.

EXAMPLE 2

2-Decarboxy-2-hydroxymethyl-4,5,6-trinor-3,7-(2'-methoxy-1',3'-interphenylene)-PGE$_1$, 1,11,15-tris(tetrahydropyranyl ether)

Solution II: A 100-ml, three-neck, round-bottomed flask, equipped with magnetic stirrer, serum stoppers and a nitrogen-vacuum connection, is charged with anhydrous diethyl ether (20 ml). The ether is alternately degassed and flushed with nitrogen (3×), then cooled to −78° C. under nitrogen and treated with 2.1 M t-butyllithium in pentane (4.33 ml).

Solution III: A 50-ml, three-neck round-bottomed flask, equipped with magnetic stirrer, serum stoppers and a nitrogen-vacuum connection, is charged with anhydrous diethyl ether (23 ml) and 2-methoxy-3-[3'-(tetrahydropyranyloxy)propyl]-1-bromobenzene (1.50 g, 4.55 mmol), and the resulting solution is alternately degassed and flushed with nitrogen (3×). The solution is cooled to −78° C. and stirred under nitrogen at that temperature for 5 minutes then transferred via double-tipped needle to a solution II at −78° C. to give a white suspension which is stirred for 1.75 hours at −78° C.

Solution I: A 250-ml, three-neck, round-bottomed flask with magnetic stirrer, serum stopper and nitrogen-vacuum connection, is charged with anhydrous diethyl ether (50 ml) and cuprous iodide (0.417 g, 2.18 mmol). The resulting suspension is alternately degassed and flushed with nitrogen (3×), then treated at ambient temperature under nitrogen with tri-n-butylphosphine (0.58 ml, 2.29 mmol). The reaction is stirred for 1 hour at ambient temperature, and the cuprous iodide gradually goes into solution. The resulting greyish solution is cooled to −78° C. and treated with solution III (at −78° C.) via double-tipped needle with positive argon pressure. The addition requires about 15 minutes, and the resulting grey suspension is stirred vigorously for an addition 45 minutes at −78° C.

The 500-ml, one-neck, round-bottomed flask which is used to concentrate the 2-methylene-4α-hydroxy-3β-[(3'S)-3'-hydroxy-trans-1'-octenyl cyclopentanone 4,3'-bis-tetrahydropyranyl ether is equipped with a magnetic stirring bar, serum stopper and a nitrogen-vacuum connection. The flask charged with 2-methylene-4α-hydroxy-3β-[(3'S)-3'-hydroxy-trans-1'-octenyl cyclopentanone 4,3'-bis-tetrahydropyranyl ether (0.37 g, 0.91 mmol) is charged with anhydrous diethyl ether (25 ml). The resulting solution is alternately degassed and flushed with nitrogen (3×), cooled to −78° C. and added to the above cuprate mixture (with vigorous stirring at −78° C.) via a double-tipped needle with positive nitrogen pressure. The addition requires 20 minutes, and the reaction mixture is then stirred at 78°

C. for an additional 45 minutes. The resulting greyish-brown reaction mixture is transferred via a ⅛-inch O.D. Teflon cannula into a rapidly stirred solution of 7.6% acetic acid/diethyl ether (100 ml) which has been pre-cooled to −60° C. After the transfer is completed, the organics are washed with brine (2×150 ml), aqueous saturated sodium bicarbonate (3×150 ml), and brine (150 ml), dried over magnesium sulfate, filtered and concentrated to 3.82 g of yellow oil. The crude product is chromatographed on silica gel (220 g) in 15% ethyl acetate/Skellysolve B. The column is eluted with 1.6 liters of 15%, 1.2 liters of 25%, and 1.75 liters of 35% ethyl acetate/Skellysolve B to give 0.46 g of the title compound.

NMR (CDCl$_3$, TMS) δ: 0.88 (t, 3H), 1.02–3.12 (m), 3.22–4.12 (m, 10H), 3.67 (s, 3H), 4.38–4.73 (m, 3H), 5.17–5.60 (m, 2H), 6.80–7.23 (m, 3H).

Infrared (film): 2941, 2870, 1745, 1467, 1455, 1440, 1365, 1323, 1260, 1200, 1135, 1121, 1077, 971, 908, 869, 767 cm$^{-1}$.

TLC (Silica Gel GF): R$_f$=0.18 in 25% ethyl acetate/hexane.

EXAMPLE 3

2-Decarboxy-2-hydroxymethyl-4,5,6-trinor-3,7-(2'-methoxy-1',3'-interphenylene)-PGF$_1$β, 1,11,15-tris(-tetra hydropyranyl ether) and 2-Decarboxy-2-hydroxymethyl-4,5,6-trinor-3,7-(2'-methoxy-1',3'-interphenylene)-PGF$_1$α, 1,11,15-tris(tetrahydropyranyl ether)

Degassed absolute methanol (7 ml) is cooled to −40° C. and treated under an inert atmosphere with sodium borohydride (0.083 g, 2.18 mmol). To the resulting suspension, a solution of the compound from Example 2 (0.43 g, 0.66 mmol) in methylene chloride (5 ml) is added. The reaction mixture is stirred for 75 minutes at −30° to −25° C., poured into ice-cold brine (60 ml) and extracted with ethyl acetate (3×60 ml). The organic extracts are washed with brine (2×60 ml), dried over magnesium sulfate, filtered and concentrated to a yellow oil (0.51 g). The crude product is chromatographed on silica gel (60 g) in 30% ethyl acetate/Skellysolve B to give 0.263 g of the PGF$_1$α title compound and 0.179 g of the PGF$_1$β title compound. PGF$_1$β deriv.:

NMR (CDCl$_3$, TMS) δ: 0.90 (t, 3H), 1.12–3.09 (m), 3.28–4.33 (m, 11H), 3.77 (s, 3H), 4.53–4.90 (m, 3H), 5.37–5.93 (m, 2H), 6.93–7.23 (m, 3H).

Infrared (film): 3455, 2930, 2865, 1465, 1455, 1440, 1350, 1320, 1255, 1200, 1180, 1135, 1116, 1075, 1035, 1015, 985, 970, 865 cm$^{-1}$.

TLC (Silica Gel GF): R$_f$=0.10 in 35% ethyl acetate/hexane. PGF$_1$α deriv.:

NMR (CDCl$_3$, TMS) δ: 0.90 (m, 3H), 1.12–3.07 (m), 3.27–4.30 (m, 12H), 3.78 (s, 3H), 4.30–4.83 (m, 3H), 5.40–5.80 (m, 2H), 6.87–7.20 (m, 3H).

Infrared (film): 3475, 2930, 2860, 1465, 1450, 1435, 1350, 1320, 1255, 1200, 1180, 1135, 1070, 1030, 1015, 970, 905, 865, 810, 767 cm$^{-1}$.

TLC (Silica Gel GF): R$_f$=0.24 in 35% ethyl acetate/hexane.

EXAMPLE 4

2-Decarboxy-2-hydroxymethyl-4,5,6-trinor-3,7-(2'-hydroxy-1',3'-interphenylene)-PGF$_1$β, 1,11,15-tris(tetrahydropyranyl ether)

Degassed hexamethylphosphoric triamide (HMPA) (8 ml) is treated at ambient temperature under an inert atmosphere with butyl mercaptan (0.33 ml). The resulting solution is cooled via ice-bath and treated dropwise with n-butyllithium (1.75 ml of 1.6 M solution). The resulting solution is stirred for a few minutes with cooling, is permitted to warm to room temperature and treated with a solution of the PGF$_1$β compound of Example 3 above (0.179 g, 0.17 mmol) in dry HMPA (4 ml). The resulting yellow solution is heated at 100°±5° C. for 2.5 hours, cooled and poured into cold, 0.2 M aqueous HCl (130 ml). The aqueous suspension is extracted with ethyl acetate (3×80 ml), and the combined ethyl acetate extracts are washed with brine (3×130 ml), dried over magnesium sulfate, filtered and concentrated to a yellow oil. The crude product is chromatographed on silica gel in 30% ethyl acetate/hexane to give 0.144 g of the title compound.

NMR (CDCl$_3$, TMS) δ: 0.87 (t, 3H), 1.10–3.17 (m), 3.20–4.27 (m, 11H), 4.43–4.88 (m, 3H), 5.30–5.87 (m, 2H), 6.60–7.00 (m, 3H), 7.17 (bs, 1H).

Infrared (film): 3370, 2930, 2870, 1595, 1465, 1440, 1375, 1355, 1325, 1265, 1240, 1200, 1140, 1118, 1075, 1035, 1025, 975, 910, 875, 815, 765 cm$^{-1}$.

TLC (Silica Gel GF): R$_f$=0.18 in 50% ethyl acetate/hexane; R$_f$=0.08 in 35% ethyl acetate/hexane.

EXAMPLE 5

2-Decarboxy-9-deoxy-2'-9α-epoxy-2-hyroxymethyl-4,5,6-trinor-3,7-(1',3'-interphenylene)-PGF$_1$, 1,11,15-tris(tetrahydropyranyl ether)

A degassed solution of the compound of Example 4 above (0.082 g, 0.127 mmol) in dry dioxane (4 ml) is treated at ambient temperature under an inert atmosphere with triphenylphosphine (0.10 g, 0.381 mmol) and diethylazodicarboxylate (63.2 μl, 0.381 mmol). The pale yellow solution is stirred for 2 hours at ambient temperature, diluted with anhydrous diethyl ether (10 ml) and stirred for 15 minutes and the reaction is concentrated in vacuo. The crude product is chromatographed on silica gel in 20% ethyl acetate/hexane to give 0.071 g of the title compound.

NMR (CDCl$_3$, TMS) δ: 0.90 (t, 3H), 1.07–3.07 (m, 36H), 3.23–4.22 (m, 10H), 4.38 (m, 1H), 4.50–4.80 (m, 3H), 5.27–5.77 (m, 2H), 6.65–7.17 (m, 3H).

Infrared (film): 3025, 2940, 2870, 1595, 1465, 1445, 1385, 1355, 1327, 1263, 1203, 1187, 1160, 1135, 1120, 1073, 1030, 975, 910, 870, 818, 765, 748 cm$^{-1}$.

TLC (Silica Gel GF): R$_f$=0.72 in 50% ethyl acetate/hexane; R$_f$=0.49 in 35% ethyl acetate/hexane.

EXAMPLE 6

2-Decarboxy-9-deoxy-2',9α-epoxy-2-hydroxymethyl-4,5,6 trinor-3,7-(1',3'-interphenylene)-PGF$_1$ A solution of the compound of Example 5 above (0.071 g, 0.113 mmol) in acetic acid (1.8 ml), water (0.9 ml), and tetrahydrofuran (0.45 ml) is reacted at 45° C. for 2.25 hours, cooled to ambient temperature, and diluted with ice-cold brine (90 ml). The aqueous suspension is extracted with ethyl acetate (3×65 ml), and the organics are washed with water (2×90 ml) and brine (2×90 ml), dried over magnesium sulfate, filtered and concentrated in vacuo. The residue is azeotroped with toluene to remove any acetic acid. The crude product is chromatographed on silica gel (25 g) in 4% methanol/ethyl acetate to give 0.034 of the title compound, m.p. 114°–116° C.

NMR (CDCl$_3$) δ: 0.90 (t, 3H), 1.08–3.25 (m, 21H), 3.40–3.70 (m, 2H), 3.77–4.20 (m, 2H), 4.37 (bs, 1H), 5.40–5.67 (m, 2H), 6.77–7.13 (m, 3H).

Mass Spec (tri-TMS derivative): Calculated for $C_{32}H_{58}O_4Si_3$:590.3643. Found: 590.3662. M/e 575, 519, 500, 429, 410, 339, 314, 261, 237, 221, 199, 173, 147, 129, 73.

TLC (Silica Gel GF): $R_f$=0.14 in ethyl acetate.

EXAMPLE 7

9-Deoxy-2'-9α,epoxy-4,5,6-trinor-3,7-(1',3'-inter phenylene)-$PGF_1$

To a three-neck, round-bottomed flask (50 ml), equipped with a magnetic stirring bar and serum stoppers, platinum oxide (0.065 g) and water (8 ml) are added. The resulting brown suspension is degassed and flushed with nitrogen (3×) then evacuated and purged with hydrogen. The suspension is reduced at atmospheric pressure for about 20 minutes until suspension turns black. The system is evacuated and flushed with nitrogen (3×) then stirred under nitrogen atmosphere for 10 minutes. The suspension is evacuated and flushed with nitrogen and removed.

The flask is equipped with a reflux condenser, a gas inlet tube (adjusted so that the tip of the tube is below the surface of the solvent), and a nitrogen connection. Oxygen gas is bubbled through the inlet tube and sodium bicarbonate (0.125 g, 1.49 mmol) is added. The suspension becomes grey, and the triol, i.e., the compound from Example 6 above, (0.055 g, 0.15 mmol) in 50% acetone/water (16 ml) is added. The suspension becomes an emulsion immediately upon the addition of the triol and the mixture is stirred vigorously at 60° C. (bath temperature) for 3.25 hours while the oxygen gas is bubbled through. The reaction is cooled to ambient temperature, ice is added, and the reaction is neutralized with 10% (aqueous) potassium bisulfate until pH ~5 to 6. The suspension is diluted with acetone (200 ml) and filtered through celite. The filter cake is washed with acetone and the combined filtrate is concentrated in vacuo. The concentrate is acidified with 10% potassium bisulfate and extracted with ethyl acetate (3×100 ml). The organics are washed with brine (2×100 ml), dried over magnesium sulfate, filtered and concentrated to an off-white solid. The crude product is recrystallized from ether-hexane to give 25 mg of off-white crystalline title product, m.p. 135°–137° C.

NMR ($CDCl_3$, TMS) δ: 0.90 (t, 3H), 1.08–3.50 (m), 3.55–4.70 (m), 5.30–5.60 (m, 2H), 6.55–7.15 (m, 3H).

Mass Spec (tris-TMS deriv.): Calculated for $C_{32}H_{56}O_5Si_3$:604.3435. Found: 604.3444. M/e 589, 533, 514, 443, 424, 353, 275, 263, 217, 173, 161, 147, 129.

EXAMPLE 8

(a) 2-Decarboxy-9-deoxy-2',9α-epoxy-2-tosyloxymethyl-4,5,6-trinor-3,7-(1',3'-interphenylene)-$PGF_1$ A solution of 2-decarboxy-9-deoxy-2',9α-epoxy-2-hydroxymethyl-4,5,6-trinor-3,7-(1',3'-interphenylene)-$PGF_1$ (0.22 g, 0.59 mmol) in dry pyridine (9 ml) is cooled to 0° C. under an inert atmosphere and treated with p-toluenesulfonyl chloride (0.126 g, 0.65 mmol). The resulting solution is stirred for 15 minutes at 0° and is allowed to react for three days at 4° C., diluted with ice-cold brine (200 ml) and extracted with ethyl acetate (3×150 ml). The organics are washed with 0.1 M aqueous hydrochloric acid (3×200 ml), saturated aqueous sodium bicarbonate (2×200 ml), and brine (2×200 ml), dried over magnesium sulfate, filtered and concentrated in vacuo. The crude product is chromatographed on silica gel in 80% ethyl acetate/hexane to give 0.056 g of the title product.

NMR ($CDCl_3$, TMS) δ: 0.90 (t, 3H), 1.07–3.37 (m, 24H), 2.43 (s, 3H), 3.70–4.23 (m, 4H). 4.37 (m, 1H), 5.43–5.67 (m, 2H), 6.70–7.07 (m, 3H), 7.40 (D, 2H), 7.83 (D, 2H).

Infrared (film): 3360, 2930, 2855, 1647, 1598, 1495, 1457, 1355, 1245, 1213, 1173, 1100, 1070, 1020, 970, 937, 890, 837, 815, 670 $cm^{-1}$.

TLC (silica gel GF): $R_f$=0.58 in ethyl acetate.

(b) 2-Decarboxy-2-cyanomethyl-9-deoxy-2',9α-epoxy-4,5,6-trinor-3,7-(1',3'-interphenylene)-$PGF_1$ A solution of the product of 1(a) above (0.12 g, 0.23 mmol) in dry dimethylformamide (8 ml) is treated at ambient temperature under an inert atmosphere with sodium cyanide (0.034 g, 0.7 mmol). The reaction is stirred at 60°–65° C. for 3.25 hours, cooled and diluted with ice-cold brine (100 ml). The resulting suspension is extracted with ethyl acetate (3×100 ml), and the organics are washed with brine (3×100 ml), dried over magnesium sulfate, filtered and concentrated to a solid (0.088 g), m.p. 110°–112° C.

NMR ($CDCl_3$, TMS) δ: (0.90, t, 3H), 1.08–3.13 (m), 4.03 (m), 4.41 (m, 1H), 5.20–5.60 (m, 2H), 6.60–7.06 (m, 3H).

Infrared (mull): 3449, 2870, 2855, 2246, 1673, 1595, 1463, 1438, 1425, 1377, 1354, 1333, 1319, 1245, 1231, 1210, 1204, 1114, 1091, 1077, 1065, 970, 963, 759, 740 $cm^{-1}$.

TLC (silica gel GF): $R_f$=0.53 in ethyl acetate.

(c) 9-Deoxy-2',9α-epoxy-2-homo-4,5,6-trinor-3,7-(1',3'-interphenylene)-$PGF_1$

A solution of the product of 1(b) above (0.088 g, 0.23 mmol-theory) in methanol (4 ml) is treated at ambient temperature with 25% potassium hydroxide/water (2 ml). The resulting solution is stirred for 18 hours at 90°–95° C., cooled to ambient temperature and diluted with 0.2 M hydrochloric acid (100 ml). The resulting suspension is extracted with ethyl acetate (3×100 ml), and the organics are washed with brine (3×100 ml), dried over magnesium sulfate, filtered and concentrated to give a yellow semi-solid.

The crude product is chromatographed on silica gel in ethyl acetate to give a white solid which is recrystalized from ether-hexane to give 0.058 g of the title compound, m.p. 150°-152° C.

NMR ($CDCl_3$, TMS) δ: 0.89 (t, 3), 1.06–3.13 (m, 20H), 3.53–4.18 (m, 2H), 4.33 (m, 1H), 4.80 (m, 3H), 5.35–5.63 (m, 2H), 6.53–7.08 (m, 3H).

Infrared (mull): 3426, 3038, 3019, 2959, 2870, 2856, 1716, 1463, 1433, 1421, 1409, 1377, 1356, 1350, 1340, 1335, 1317, 1257, 1243, 1208, 1187, 1121, 972, 918, 763, 737 $cm^{-1}$.

TLC (silica gel GF): $R_f$=0.00–0.20 in ethyl acetate. $R_f$=0.41 in the organic phase of 9:2:5:10 EtOAc-HOAc-water-cyclohexane.

EXAMPLE 9

When in the procedure of Example 2 one substitutes
2-methylene-4α-hydroxy-3β-[(3'S)-3'-hydroxyoctanyl]-cyclopentanone 4,3'-bis(tetrahydropyranyl ether),
2-methylene-4α-hydroxy-3β-[(3'S)-3'-hydroxy-1-octynyl]cyclopentanone 4,3'-bis(tetrahydropyranyl ether),
2-methylene-4α-hydroxy-3β-[(3'S)-3'-hydroxy-1-methyl-oct-6-yn-1-enyl]cyclopentanone 4,3'-bis(tetrahydropyranyl ether), 2-methylene-4α-hydroxy-3β-[(3'S)-3'-hydroxy-4'-phenyl-1-butenyl]cyclopentanone 4,3'-bis(tetrahydropyranyl ether), 2-methylene-4α-hydroxy-3β-[(3'S)-3'-hydroxy-3'-phenoxy-1-propenyl]cyclopentanone 4,3'-bis(tetrahydropyranyl ether), 2-methylene-4α-hydroxy-3β-[(3'S)-3'-hydroxy-4'-(3-thienyl)-1-butenyl]cyclopentanone 4,3'-bis(tetrahydropyranyl ether), 2-methylene-4α-hydroxy-3β-[(3'S)-3'-hydroxy-3'-phenyl)-1-propenyl]cyclopentanone 4,3'bis(tetrahydropyranyl ether), 2-methylene 4α-hydroxy-3β-[(3'S)-3'-hydroxy-3'-cyclohexyl-1-propenyl]cyclopentanone 4,3'-bis(tetrahydropyranyl ether), 2-methylene-4α-hydroxy-3β-[(3'S)-3'-hydroxy-4'-(3-thienyloxy)-1-butenyl]cyclopentanone 4,3'-bis(tetrahydropyranyl ether), or 2-methylene-4α-hydroxy-3β-[(3'S)-3'-hydroxy-3'-(2-ethylcyclobutyl)-1-propenyl]cyclopentanone 4,3'-bis(tetrahydropyranyl ether)

which are prepared as generally described in Examples 1, 2, 3 and 4 of U.S. Pat. No. 4,181,798 for 2-methylene-4α-hydroxy-3β-[(3'S)-3'-hydroxy-trans-1'-octenyl]cyclopentanone 4,3'-bis(tetrahydropyranyl ether) in Solution 1 and follows the procedure of Example 2 the following compounds are obtained:

2-decarboxy-2-hydroxymethyl-4,5,6-trinor-3,7-(2'-methoxy-1',3'-interphenylene)-13,14-dihydro-PGE$_1$, 2,11,15-tris(tetrahydropyranyl ether), 2-decarboxy-2-hydroxymethyl-4,5,6-trinor-3,7-(2'-methoxy-1',3'-interphenylene)-13,14-dehydro-PGE$_1$, 2,11,15-tris(tetrahydropyranyl ether), 2-decarboxy-2-hydroxymethyl-4,5,6-trinor-3,7-(2'-methoxy-1',3'-interphenylene)-16-methyl-18,19-tetradehydro-PGE$_1$, 2,11,15-tris(tetrahydropyranyl ether), 2-decarboxy-2-hydroxymethyl-4,5,6-trinor-3,7-(2'-methoxy-1',3'-interphenylene)-17,18,19,20-tetranor-16-phenyl-PGE$_1$, 2,11,15-tris(tetrahydropyranyl ether), 2-decarboxy-2-hydroxymethyl-4,5,6-trinor-3,7-(2'-methoxy-1',3'-interphenylene)-16,17,18,19,20-pentanor-15-phenoxy-PGE$_1$, 2,11,15-tris(tetrahydropyranyl ether), 2-decarboxy-2-hydroxymethyl-4,5,6-trinor-3,7-(2'-methoxy-1',3'-interphenylene)-17,18,19,20-tetranor-16-(3-thienyl)-PGE$_1$, 2,11,15-tris(tetrahydropyranyl ether), 2-decarboxy-2-hydroxymethyl-4,5,6-trinor-3,7-(2'-methoxy-1',3'-interphenylene)-16,17,18,19,20-pentanor-15-phenyl-PGE$_1$, 2,11,15-tris(tetrahydropyranyl ether), 2-decarboxy-2-hydroxymethyl-4,5,6-trinor-3,7-(2'-methoxy-1',3'-interphenylene)-16,17,18,19,20-pentanor-15-cyclohexyl-PGE$_1$, 2,11,15-tris(tetrahydropyranyl ether), 2-decarboxy-2-hydroxymethyl-4,5,6-trinor-3,7-(2'-methoxy-1',3'-interphenylene)-17,18,19,20-tetranor-16-(2-thienyloxy)-PGE$_1$, 2,11,15-tris(tetrahydropyranyl ether), and 2-decarboxy-2-hydroxymethyl-4,5,6-trinor-3,7-(2'-methoxy-1',3'-interphenylene)-16,17,18,19,20-pentanor-15-(2-ethylcyclobutyl)-PGE$_1$, 2,11,15-tris(tetrahydropyranyl ether).

EXAMPLE 10

When one substitutes appropriate amounts of each of the PGE$_1$ compounds of Example 9 for 2-decarboxy-2-hydroxymethyl-4,5,6-trinor-3,7-(2'-methoxy-1',3'-interphenylene)-PGE$_1$, 2,11,15-tris(tetrahydropyranyl ether) in Example 3 one obtains the respective PGF$_1$α and PGF$_1$β compounds wherein the lower side chain correspond to the PGE$_1$ compounds of Example 9, when the thus obtained PGF$_1$β compounds are substituted for 2-decarboxy-2-hydroxymethyl-4,5,6-trinor-3,7-(2'-methoxy-1',3'-interphenylene)-PGF$_1$β in the procedure of Example 4 one obtains the corresponding 2-decarboxy-2-hydroxymethyl-4,5,6-trinor-3,7-(2'-hydroxy-1',3'-interphenylene)-PGF$_1$β, 2,11,15-tris(tetrahydropyranyl ether) derivatives wherein the lower side chain corresponds to that of the PGE$_1$ compounds of Example 9. When the thus obtained "2'-hydroxy-1',3'-interphenylene derivatives are substituted for the compound of Example 4 in the procedure of Example 5 one obtains the following compounds.

2-decarboxy-9-deoxy-2',9α-epoxy-2-hydroxymethyl-4,5,6-trinor-3,7-(1',3'-interphenylene)-13,14-dihydro-PGF$_1$, 2,11,15-tris-(tetra hydropyranyl ether), 2-decarboxy-9-deoxy-2',9α-epoxy-2-hydroxymethyl-4,5,6-trinor-3,7-(1',3'-interphenylene)-13,14-dehydro-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-16-methyl-18,19-tetradehydro-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-17,18,19,20-tetranor-16-phenyl-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-16,17,18,19,20-pentanor-15-phenoxy-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-17,18,19,20-tetranor-16-(3-thienyl)-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-16,17,18,19,20-pentanor-15-phenyl-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-16,17,18,19,20-pentanor-15-cyclohexyl-PGF$_1$, 2,11,15-tris-(tetrahydropyranyl ether), 2-decarboxy-9-deoxy-2',9α-epoxy-2-hydroxymethyl-4,5,6-trinor-3,7-(1',3'-interphenylene)-17,18,19,20-tetranor-16-(2-thienyloxy)-PGF$_1$, 2,11,15-tris-(tetrahydropyranyl ether), and 2-decarboxy-9-deoxy-2',9α-epoxy-2-hydroxymethyl-4,5,6-trinor-3,7-(1',3'-interphenylene)-16,17,18,19,20-pentanor-15-(2-ethylcyclobutyl)-PGF$_1$, 2,11,15-tris-(tetrahydropyranyl ether).

When the thus obtained above named PGF$_1$ compounds are substituted for the compound of Example 5 in the procedure of Example 6 the corresponding hydroxy deprotected products are obtained all of which are converted to the corresponding C-1 carboxylic acid derivative when substituted for the compound of Example 6 in the procedure of Example 7.

EXAMPLE 11

When 2-methoxy-3-[3'-(tetrahydropyranyloxypropoxy]-1-bromo-benzene, prepared from 3-bromo-2-methoxyphenoxyacetic acid methyl ester, is substituted for 2-methoxy-3-[3'-(tetrahydropyranyloxypropyl)-1-bromobenzene in the procedure of Example 2, one obtains 2-decarboxy-2-hydroxymethyl-4,5,6-trinor-3-oxa-3,7-(2'-methoxy-1',3'-interphenylene)-PGE$_1$, 2,11,15-tris(tetrahydropyranyl ether) which when substituted for the compound of Example 2 in the procedure of Example 3 gives the corresponding PGF$_1\alpha$ and PGF$_1\beta$ compounds. When the thus obtained PGF$_1\beta$ compound is substituted for the PGF$_1\beta$ compound of Example 3 in the procedure of Example 4 one obtains 2-decarboxy-2-hydroxymethyl-4,5,6-trinor-3-oxa-3,7-(2'-hydroxy-1',3'-interphenylene)-PGF$_1\beta$, 2,11,15-tris(tetrahydropyranyl ether) which when substituted for the compound of Example 4 in the procedure of Example 5 gives 2-decarboxy-9-deoxy-2',9$\alpha$-epoxy-2-hydroxymethyl-4,5,6-trinor-3-oxa-3,7-(1',3'-interphenylene)-PGF$_1$, 2,11,15-tris(tetrahydropyranyl ether) which is deprotected by the procedure of Example 6 to give 2-decarboxy-9-deoxy-2',9$\alpha$-epoxy-2-hydroxymethyl-4,5,6-trinor-3-oxa-3,7-(1',3'-interphenylene)-PGF$_1$ which can be oxidized to the corresponding C-1 carboxylic acid by the procedure of Example 7 to give 9-deoxy-2',9$\alpha$-epoxy-4,5,6-trinor-3-oxa-3,7-(1',3'-interphenylene)-PGF$_1$.

EXAMPLE 12

When one substitutes 2-methoxy-3-[2',2'-difluoro-3'-(tetrahydropyranyloxypropyl]-1-bromobenzene, prepared as depicted in Chart E, for 2-methoxy-3-[3'-tetrahydropyranyloxypropyl]-1-bromobenzene in the procedure of Example 2 and substitutes the product thus obtained for Example 2 in the procedure of Example 3 and continues the sequence as described in Example 11 through Example 6 one obtains 2-decarboxy-2-deoxy-2',9$\alpha$-epoxy-2-hydroxymethyl-2,2-difluoro-4,5,6-trinor-3,7-(1',3'-interphenylene)-PGF$_1$ which can be oxidized to the corresponding C-1 carboxylic acid derivative by the procedure of Example 7.

EXAMPLE 13

When 2-methoxy-3-tetrahydropyranyloxy-1-bromobenzene is substituted for 2-methoxy-3-[3'-(tetrahydropyranyloxypropyl)]-1-bromobenzene in the procedure of Example 2, one obtains 1,2,4,5,6-pentanor-3-oxa-3,7-(2'-methoxy-1',3'-interphenylene)-PGE$_1$, 3,11,15-tris(tetrahydropyranyl ether) which when substituted for the compound of Example 2 in the procedure of Example 3 gives the corresponding PGF$_1\alpha$ and PGF$_1\beta$ compounds. When the thus obtained PGF$_1\beta$ compound is substituted for the PGF$_1\beta$ compound of Example 3 in the procedure of Example 4 one obtains 1,2,4,5,6-pentanor-3-oxa-3,7-(2'-hydroxy-1',3'-interphenylene)-PGF$_1\beta$, 3,11,15-tris(tetrahydropyranyl ether) which when substituted for the compound of Example 4 in the procedure of Example 5 gives 9-deoxy-2',9$\alpha$-epoxy-1,2,4,5,6-pentanor-3-oxa-3,7-(1',3'-interphenylene)-PGF$_1$, 3,11,15-tris(tetrahydropyranyl ether) which is deprotected by the procedure of Example 6 to give 9-deoxy-2',9$\alpha$-epoxy-1,2,4,5,6-pentanor-3-oxa-3,7-(1',3'-interphenylene)-PGF$_1$. Treatment of 9-deoxy-2',9$\alpha$-epoxy-1,2,4,5,6-pentanor-3-oxa-3,7-(1',3'-interphenylene)-PGF$_1$ with one equivalent of sodium hydride and one equivalent of methylbromoacetate in glyme at 0° C. for several hours followed by partitioning between ethyl acetate and brine followed by removal of solvents (i.e., ethyl acetate and glyme) affords 9-deoxy-2',9$\alpha$-epoxy-3-oxa-4,5,6-trinor-3,7-(1',3'-interphenylene)-PGF$_1$, methyl ester. Hydrolysis of 9-deoxy-2',9$\alpha$-epoxy-3-oxa-4,5,6-trinor-3,7-(1',3'-interphenylene)-PGF$_1$, methyl ester with 5% potassium hydroxide in 9:1 methanol/water at room temperature for several hours followed by acidification and extraction into ethyl acetate followed by removal of solvent affords 9-deoxy-2',9$\alpha$-epoxy-3-oxa-4,5,6-trinor-3,7-(1',3'- interphenylene)-PGF$_1$.

EXAMPLE 14

A solution of 3.0 g of 6-allyl-2-bromophenol (from Example 1(a)) in 17 ml dry glyme is added to 1.65 g potassium t-butoxide in 22 ml t-butanol. The resulting suspension is treated with 3.2 ml methyl iodide and stirred overnight at room temperature, diluted with water, and extracted into ether. The solvents are removed in vacuo and the residue chromatographed on basic alumina to give (after distillation at 0.45 mm at 113° C.) 1.76 g of 2-bromo-6-(1'-propenyl)-anisole (TLC R$_f$ 0.62 in 5% ethyl acetate in hexane).

A solution of 0.38 g of the above 2-bromo-6-(1'-propenyl)-anisole in 55 ml of methanol at −78° C. is treated with ozone for 8 minutes, then treated with 24 ml dimethylsulfide and let stand at 0° C. overnight, diluted with ethyl acetate, and washed with brine, saturated aqueous sodium bicarbonate, and brine. The solvents are removed in vacuo to give 2-bromo-6-formyl-anisole (TLC R$_f$ 0.39 in 10% ethyl acetate in hexanol).

A solution of 0.037 g 2-bromo-6-formyl-anisole in 1 ml methylene chloride is treated with 0.54 sodium dibasic phosphate and 1.3 ml trifluoroperacetic acid, stirred overnight, treated with 10% aqueous sodium carbonate (5 ml) and 5 ml diethyl ether, stirred for 1.5 hours, and partitioned between water and ether. The ether portion is extracted with 1 N aqueous sodium hydroxide, the hydroxide extracts acidified and then extracted with ether. Concentration of the ether extracts affords 3-bromo-2-methoxyphenol.

Treatment of 3-bromo-2-methoxyphenol with dihydropyran and an acid catalyst as described herein affords 2-methoxy-3-tetrahydropyranyloxy-1-bromobenzene.

EXAMPLE 15

A solution of 0.25 g of 9-deoxy-2',9$\alpha$-epoxy-4,5,6-trinor-3,7-(1',3'-interphenylene)-PGF$_1$, 0.45 ml diisopropylethylamine, and 0.82 ml methyl iodide in 7.5 ml acetonitrile is stirred at room temperature overnight, diluted with ethyl acetate, washed with 5% aqueous sodium sulfite and then with brine. Removal of solvents from the ethyl acetate extract affords 0.23 g of 9-deoxy-2',9$\alpha$-epoxy-4,5,6-trinor-3,7-(1',3'-interphenylene)-PGF$_1$, methyl ester which is dissolved in 4 ml dimethylformamide and treated with 0.345 g t-butyldimethylsilyl chloride and 0.31 g of imidazole, then stirred at room temperature overnight, diluted with ice-cold brine and extracted with ethyl acetate. Concentration of the ethyl acetate extract followed by chromatography on silica gel affords 0.32 g of 9-deoxy-2',9$\alpha$-epoxy-4,5,6-trinor-3,7-(1',3'-interphenylene)-PGF$_1$, methyl ester, 11,15-bis(t-butyldimethyl silyl ether) (TLC R$_f$ at 0.71 in 20% ethyl acetate/hexane).

A solution of 0.23 g of N-isopropylcyclohexylamine in 5 ml of dry tetrahydrofuran at −78° C. under an inert atmosphere is treated with 1.18 ml of 1.3 M n-butyllithium in hexane, stirred at −78° C. for 15 minutes, treated with 0.32 g of 9-deoxy-2',9α-epoxy-4,5,6-trinor-3,7-(1',3'-interphenylene)-PGF₁, methyl ester, 11,15-bis(t-butyldimethyl silyl ether) in 4 ml of tetrahydrofuran, stirred for 45 minutes at −78° C., treated with 0.32 g of diphenyl diselenide in 4 ml of tetrahydrofuran, stirred for one hour at −78° C., warmed to room temperature, quenched with ammonium chloride solution, and extracted with diethyl ether. Chromatography on silica gel affords 0.17 g of the corresponding 2-selenophenyl derivative, which is dissolved in 5 ml of methylene chloride, treated with 0.17 ml of 30% aqueous hydrogen peroxide and 0.6 ml of water, stirred at room temperature for one hour, diluted with methylene chloride, and washed with saturated aqueous sodium bicarbonate and brine. Removal of solvents followed by chromatography affords 9-deoxy-2',9α-epoxy-2,3-didehydro-4,5,6-trinor-3,7-(1',3'-interphenylene)-PGF₁, methyl ester, (11,15-bis(t-butyldimethyl ether), which when treated with tetra-n-butylammonium fluoride in tetrahydrofuran (as described herein to remove silyl protecting groups at C-11 and C-15) followed by 5% potassium hydroxide in 9:1 methanol-water hydrolysis of the methyl ester affords 9-deoxy-2',9α-epoxy-2,3-didehydro-4,5,6-trinor-3,7-(1',3'-interphenylene)-PGF₁.

FORMULA CHART

Formula I

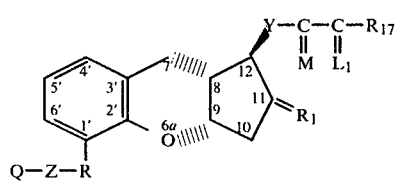

Formula XVI

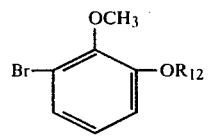

Formula XVIII

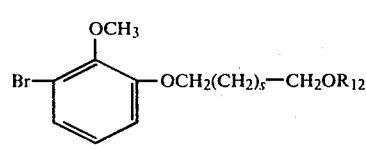

CHART A

Formula II

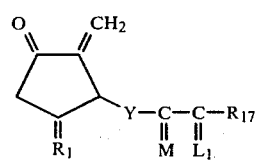

Formula III

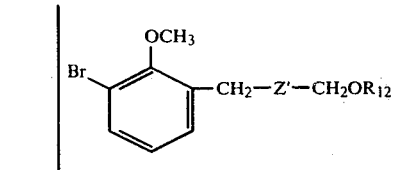

-continued
CHART A

Formula IV

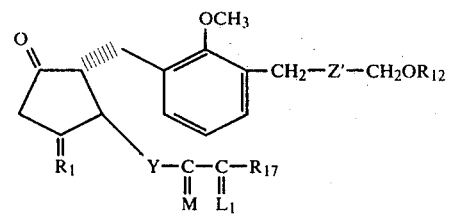

Formula V

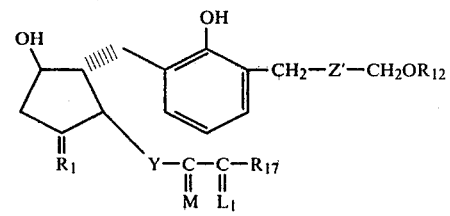

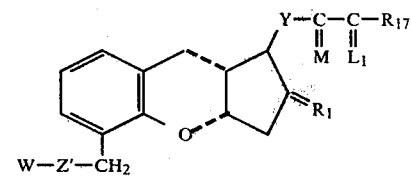

| Formula | W |
|---|---|
| VI | —CH₂OR₁₂ |
| VII | —CH₂OH |
| VIII | Q' |

CHART B

Formula IX

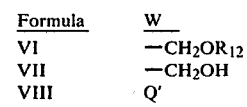

Formula X

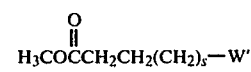

Formula XI

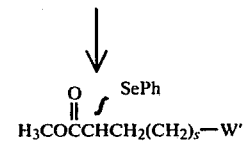

Formula XII

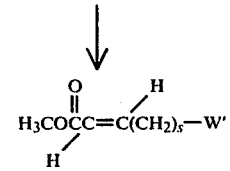
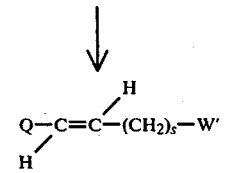

-continued
CHART B
W' is
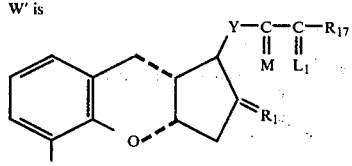
CHART C
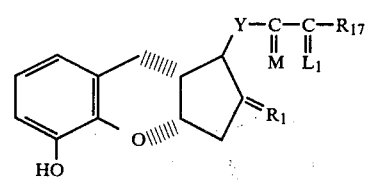
Formula XIII
↓
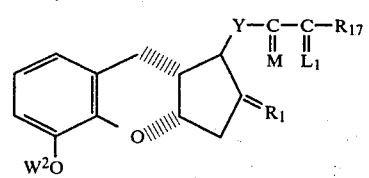
| Formula | $W^2$ |
|---|---|
| XIV | —Z'—COOalkyl |
| XV | —Z'—Q |
| XVII | $R_{12}$ |
CHART D
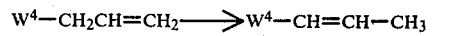
Formula D-1    Formula D-9
↓
Formula D-2    Formula D-3
↓
Formula D-4
↓
Formula D-5
↓
Formula D-6
↓
-continued
CHART D
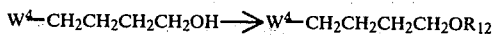
Formula D-7    Formula D-8
$W^4$ is
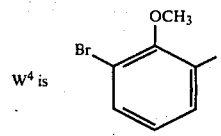
CHART E
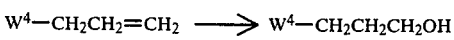
Formula E-1    Formula E-2
↓
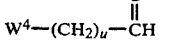
Formula E-3
↓
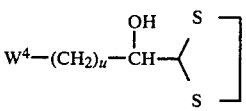    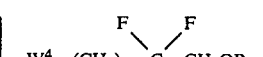
Formula E-4    Formula E-11
↓    ↑
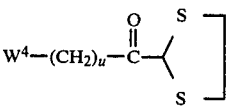    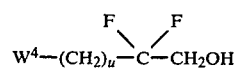
Formula E-5    Formula E-10
↓    ↑
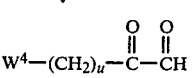    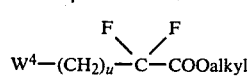
Formula E-6    Formula E-9
↓    ↑
    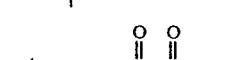
Formula E-7    Formula E-8
$W^4$ is
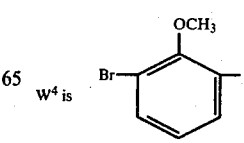

CHART F

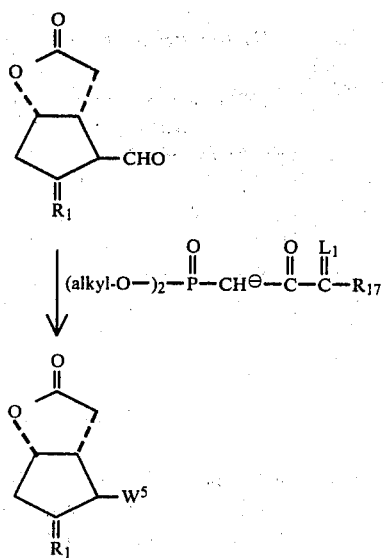

Formula F-1

Formula F-2

Formula F-3

CHART G

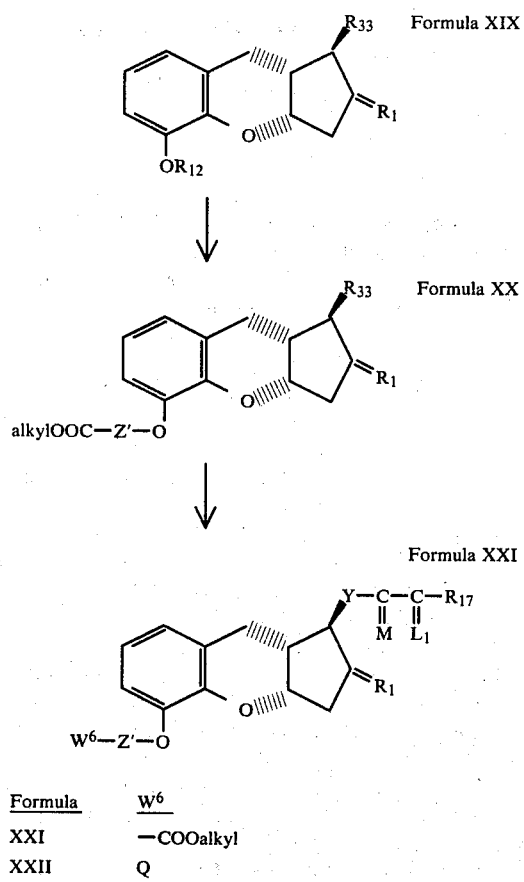

Formula XIX

Formula XX

Formula XXI

| Formula | $W^6$ |
|---|---|
| XXI | —COOalkyl |
| XXII | Q |

I claim:

1. A compound of the formula

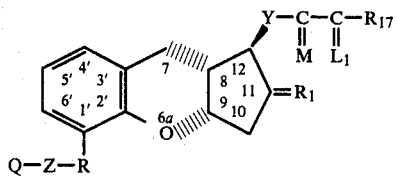

wherein R is —CH$_2$— or —O—; wherein Z is —CH$_2$—; —CH$_2$CH$_2$—; —CF$_2$—; —CF$_2$CH$_2$; or wherein —Z—R— taken together is trans—CH=CH—CH$_2$— or trans—CH=CH—;
wherein Q is
(1) —COOR$_5$, wherein R$_5$ is
  (a) hydrogen,
  (b) (C$_1$-C$_{12}$)alkyl,
  (c) (C$_3$-C$_{10}$)cycloalkyl,
  (d) (C$_7$-C$_{12}$)aralkyl,
  (e) phenyl optionally substituted with one, 2 or 3 chloro or (C$_1$-C$_4$)alkyl,
  (f) phenyl substituted in the para-position with —NHCOR$_6$, —COR$_7$, —OC(O)R$_8$ or —CH=N—NHCONH$_2$, wherein R$_6$ is methyl, phenyl, acetamidophenyl, ,enzamidophenyl or —NH$_2$; R$_7$ is methyl, phenyl, —NH$_2$, or methoxy; and R$_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2-yl)-2-oxopropan-1-yl P-oxide, or
  (j) a pharmacologically acceptable cation;
(2) —CH$_2$OH;
(3) —COL$_2$, wherein L$_2$ is
  (a) an amino group of the formula —NR$_9$R$_{10}$ wherein R$_9$ is hydrogen or (C$_1$-C$_{12}$)alkyl and R$_{10}$ is
    (i) hydrogen
    (ii) (C$_1$-C$_{12}$)alkyl
    (iii) (C$_3$-C$_{10}$)cycloalkyl,
    (iv) (C$_7$-C$_{12}$)aralkyl
    (v) phenyl optionally substituted with one, 2 or 3 chloro, (C$_1$-C$_3$)alkyl, hydroxy, carboxy, (C$_2$-C$_5$)alkoxycarbonyl, or nitro,
    (vi) (C$_2$-C$_5$)carboxyalkyl,
    (vii) (C$_2$-C$_5$)carbamoylalkyl,
    (viii) (C$_2$-C$_5$)cyanoalkyl,
    (ix) (C$_3$-C$_6$)acetylalkyl,
    (x) (C$_7$-C$_{12}$)benzoylalkyl, optionally substituted by one, 2, or 3 chloro, (C$_1$-C$_3$)alkyl, hydroxy, (C$_1$-C$_3$)alkoxy, carboxy, (C$_2$-C$_5$)-alkoxycarbonyl, or nitro,
    (xi) pyridyl, optionally substituted by one, 2, or 3 chloro, (C$_1$-C$_3$)alkyl, or (C$_1$-C$_3$)alkoxy,
    (xii) (C$_6$-C$_9$)pyridylalkyl optionally substituted by one, 2, or 3 chloro, (C$_1$-C$_3$)alkyl, hydroxy, or (C$_1$-C$_3$)alkyl,
    (xiii) (C$_1$-C$_4$)hydroxyalkyl,
    (xiv) (C$_1$-C$_4$)dihydroxyalkyl,
    (xv) (C$_1$-C$_4$)trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 (C$_1$-C$_{12}$)alkyl;

(c) carbonylamino of the formula —NH$_{11}$COR$_{10}$, wherein R$_{11}$ is hydrogen or (C$_1$–C$_4$)alkyl and R$_{10}$ is other than hydrogen, but otherwise defined as above;

(d) sulfonylamino of the formula —NR$_{11}$SO$_2$R$_{10}$, wherein R$_{11}$ and R$_{10}$ are defined in (c);

(4) —CH$_2$NL$_3$L$_4$, wherein L$_3$ and L$_4$ are hydrogen or (C$_1$–C$_4$)alkyl, being the same or different, or the pharmacologically acceptable acid addition salts thereof when Q is —CH$_2$NL$_3$L$_4$;

(5) —CN;

(6) 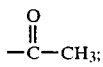
—C—CH$_3$;

wherein R$_1$ is oxo; H,H; α-OR$_{12}$,β-H; α-H,β-OR$_{12}$; α-CH$_2$OR$_{12}$,β-H; α-H,β-CH$_2$OR$_{12}$ wherein R$_{12}$ is hydrogen or a hydroxyl protective group;

wherein Y is trans —CH=CH—, cis—CH=CH—, —CH$_2$CH$_2$—, or —C≡C—;

wherein M is α-OR$_{12}$,β-R$_{14}$; or α-R$_{14}$,β-OR$_{12}$, wherein R$_{12}$ is as defined above, and R$_{14}$ is hydrogen or methyl;

wherein L$_1$ is α-R$_{15}$,β-R$_{16}$; α-R$_{16}$,β-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;

wherein R$_{17}$ is (1) —C$_m$H$_{2m}$CH$_3$ wherein m is an integer of from one to 5, (2) phenoxy optionally substituted by one, 2, or 3 chloro, fluoro, trifluoromethyl, (C$_1$–C$_3$)alkyl, or (C$_1$–C$_3$)alkoxy, with the proviso that not more than two substituents are other than alkyl and with the proviso that R$_{17}$ is phenoxy or substituted phenoxy, only when R$_{15}$ and R$_{16}$ are hydrogen or methyl, being the same or different;

(3) phenyl, benzyl, phenylethyl, or phenylpropyl optionally substituted on the aromatic ring by one, 2, or 3 chloro, fluoro, trifluoromethyl (C$_1$–C$_3$)alkyl, or (C$_1$–C$_3$)alkoxy, with the proviso that not more than two substituents are other than alkyl, (4) cis—CH=CH—CH$_2$CH$_3$, (5) —(CH$_2$)$_2$—CH(OH)—CH$_3$, (6) —(CH$_2$)$_3$—CH=C(CH$_3$)$_2$, (7) 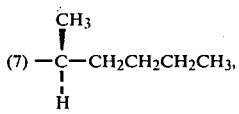

(8) 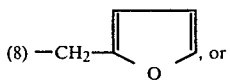, or (9) 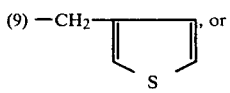, or wherein —C—R$_{17}$ taken together is
   ‖
   L$_1$ (1) (C$_4$–C$_7$)cycloalkyl optionally substituted by one to 3 (C$_1$–C$_5$)alkyl, (2) 3-thienyloxymethyl, (3) 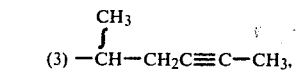

(4) —C≡C—C$_q$H$_{2q}$CH$_3$ wherein q is an integer of from 2 to 6, or (5) —C$_p$H$_{2p}$CH=CH$_2$ wherein p is an integer of from 3 to 7; and individual optical isomers thereof.

2. A compound of claim 1 wherein R$_{12}$ is hydrogen or a pharmacologically acceptable salt thereof.

3. A compound of claim 2 wherein Y is trans—CH=CH—, —C≡C, or —CH$_2$CH$_2$—.

4. A compound of claim 3 wherein Q is —COOR$_5$, COL$_2$ wherein L$_2$ is an amine group of the formula —NR$_9$R$_{10}$, or

—CCH$_3$.

5. A compound of claim 4 wherein R$_{17}$ is —C$_m$H$_{2m}$CH$_3$ wherein m is an integer of from one to 5; phenoxy; phenyl; benzyl; or 3-thienylmethyl; or wherein

—C—R$_{17}$
 ‖
 L$_1$ taken together is cyclohexyl; 3-ethylcyclobutyl; 3-thienyloxymethyl;

or 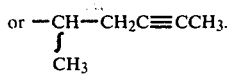

6. A compound of claim 5 wherein R$_5$ is hydrogen, a pharmacologically acceptable cation, methyl or ethyl, and R$_{17}$ is —C$_m$H$_{2m}$CH$_3$ wherein m is an integer of from one to 5 carbon atoms or wherein

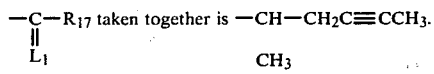

7. A compound of claim 3 or 6 wherein Z is —CH$_2$— or —CF$_2$—.

8. A compound of claim 7 wherein R is oxa.

9. A compound of claim 1 which is 2-decarboxy-9-deoxy-2',9α-epoxy-2-hydroxymethyl-4,5,6-trinor-3,7-(1',3'-interphenylene)-PGF$_1$.

10. A compound of claim 1 which is 9-deoxy-2'-9α,epoxy-4,5,6-trinor-3,7-(1',3'-interphenylene)-PGF$_1$.

11. A compound of claim 1 which is 2-decarboxy-2-cyanomethyl-9-deoxy-2',9α,epoxy-4,5,6-trinor-3,7-(1',3'-interphenylene)-PGF$_1$.

12. A compound of claim 1 which is 9-deoxy-2',9α,epoxy-2-homo-4,5,6-trinor-3,7-(1',3'-interphenylene)-PGF$_1$.

13. A compound of claim 1 which is 9-deoxy-2',9α-epoxy-2,3-didehydro-4,5,6-trinor-3,7-(1',3'-interphenylene)-PGF$_1$.

14. A compound of the formula

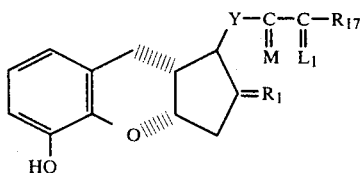

or

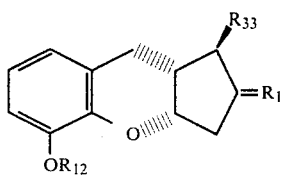

wherein $R_1$ is oxo; H,H; $\alpha$-$OR_{12}$,$\beta$-H; $\alpha$-H,$\beta$-$OR_{12}$; $\alpha$-$CH_2OR_{12}$,$\beta$-H; $\alpha$-H,$\beta$-$CH_2OR_{12}$ wherein $R_{12}$ is hydrogen or a hydroxyl protective group;
  wherein Y is trans —CH=CH—, cis—CH=CH—, —$CH_2CH_2$—, or —C≡C—;
  wherein M is $\alpha$-$OR_{12}$,$\beta$-$R_{14}$; or $\alpha$-$R_{14}$,$\beta$-$OR_{12}$, wherein $R_{12}$ is as defined above, and $R_{14}$ is hydrogen or methyl;
  wherein $L_1$ is $\alpha$-$R_{15}$,$\beta$-$R_{16}$; $\alpha$-$R_{16}$,$\beta$-$R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro; wherein $R_{17}$ is

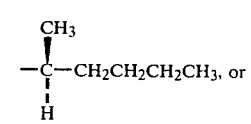

wherein $-\underset{\underset{L_1}{\|}}{C}-R_{17}$ taken together is (1) $-\overset{CH_3}{\underset{\int}{C}H}-CH_2C\equiv C-CH_3$, (2) —C≡C—$C_qH_{2q}CH_3$ wherein q is an integer of from 2 to 6, or (3) —$C_pH_{2p}$CH=$CH_2$ wherein p is an integer of from 3 to 7; wherein $R_{12}$ is hydrogen or a hydroxyl protecting group; wherein $R_{33}$ is

or —$CH_2OR_{12}$ wherein $R_{12}$ has the meaning defined above; and individual optical isomers thereof.

* * * * *